US012521159B2

(12) United States Patent
Terziotti et al.

(10) Patent No.: US 12,521,159 B2

(45) Date of Patent: Jan. 13, 2026

(54) DUAL-PURPOSE ORTHOPEDIC SURGERY INSTRUMENT

(71) Applicant: Joint Development, Inc., Salt Lake City, UT (US)

(72) Inventors: Luca Terziotti, Salt Lake City, UT (US); Dermott J. McHugh, Salt Lake City, UT (US); Eric M. Dacus, Salt Lake City, UT (US)

(73) Assignee: Joint Development, Inc., Salt Lake City, UT (US)

( * ) Notice: Subject to any disclaimer, the term of this patent is extended or adjusted under 35 U.S.C. 154(b) by 490 days.

(21) Appl. No.: 17/977,988

(22) Filed: Oct. 31, 2022

(65) Prior Publication Data

US 2023/0139058 A1 May 4, 2023

Related U.S. Application Data

(60) Provisional application No. 63/273,726, filed on Oct. 29, 2021.

(51) Int. Cl.
*A61B 17/92* (2006.01)

(52) U.S. Cl.
CPC ........ *A61B 17/92* (2013.01); *A61B 2017/925* (2013.01)

(58) Field of Classification Search
CPC ............... A61B 17/92; A61B 2017/922; A61F 2002/4681; B25D 1/16
USPC ............................................................. 81/27
See application file for complete search history.

(56) References Cited

U.S. PATENT DOCUMENTS

| | | | | | |
|---|---|---|---|---|---|
| 532,008 | A * | 1/1895 | Neu | B25D 1/16 | 254/113 |
| 593,942 | A * | 11/1897 | Johnson | B25D 1/16 | 81/27 |
| 4,971,479 | A * | 11/1990 | Byers, Sr. | E01F 9/608 | 173/90 |
| 5,248,002 | A * | 9/1993 | Williams | H01R 4/66 | 173/90 |
| 5,365,648 | A * | 11/1994 | Fuga | B25D 1/02 | 29/254 |
| 5,476,467 | A * | 12/1995 | Benoist | A61B 17/92 | 606/100 |
| 5,788,701 | A * | 8/1998 | McCue | A61B 17/1604 | 606/88 |
| 6,592,590 | B2 * | 7/2003 | Simon | A61B 17/921 | 173/90 |

(Continued)

*Primary Examiner* — David W Bates

(74) *Attorney, Agent, or Firm* — Lowry Blixseth APC; Scott M. Lowry

(57) ABSTRACT

The dual-purpose orthopedic instrument includes an elongated body, an impactor block formed from a first end of the elongated body selectively couplable with a modular impactor head and a strike block formed from a second end of the elongated body including a strike surface for selectively receiving a strike force thereof. An externally accessible channel formed within the elongated body has a size and shape for pass-through reception and select retention of an extractor rod therein. As such, the elongated body is usable as a modular impactor when the impactor block is selectively coupled with the impactor head and as a weight of a slap hammer when selectively coupled with the extractor rod in slidable relation relative thereto.

36 Claims, 18 Drawing Sheets

(56) References Cited

U.S. PATENT DOCUMENTS

| | | | | | |
|---|---|---|---|---|---|
| 6,814,738 | B2 * | 11/2004 | Naughton | A61F 2/4603 606/100 |
| 8,080,015 | B2 * | 12/2011 | Buttler | B25D 1/14 173/90 |
| 8,486,084 | B2 * | 7/2013 | Huene | A61B 17/92 606/100 |
| 9,254,159 | B2 * | 2/2016 | Li | A61B 17/8866 |
| 10,695,194 | B2 * | 6/2020 | Robinson | A61F 2/4611 |
| 11,903,848 | B2 * | 2/2024 | Beyer | A61F 2/4611 |
| 2005/0240197 | A1 * | 10/2005 | Kmiec, Jr. | A61B 17/921 606/100 |
| 2006/0128673 | A1 * | 6/2006 | Firnges | A61P 3/04 514/149 |
| 2012/0143204 | A1 * | 6/2012 | Blaylock | A61F 2/461 623/20.35 |
| 2013/0204265 | A1 * | 8/2013 | Capek | A61B 17/92 606/99 |
| 2018/0140438 | A1 * | 5/2018 | Robinson | A61F 2/4611 |
| 2020/0229857 | A1 * | 7/2020 | Sweitzer | A61F 2/4603 |
| 2023/0303296 | A1 * | 9/2023 | Reuter | B01D 29/35 |

* cited by examiner

DUAL-PURPOSE ORTHOPEDIC SURGERY INSTRUMENT

BACKGROUND OF THE INVENTION

The present invention generally relates to a dual-purpose orthopedic surgery instrument. More specifically, the dual-purpose orthopedic surgery instrument doubles as a modular impactor alone and as a weight component of a slap hammer when combined with an extractor.

Knee arthroplasty requires numerous instruments to prepare the tibia and femur for knee replacement components, and insertion and/or extraction of those components. For example, once the proximal end of the tibia is resected, a surgeon may use a tibial trial component to determine what size tibial component should be implanted as part of the orthopedic surgical procedure. The trial component also ensures that proper cuts were made during resection and notifies the surgeon if further alterations are required. Trial components are inserted via an impactor instrument that includes a handle with an impactor head on one end and a strike plate on the other. Generally, a surgeon will locate the impactor head on the trial component and impart a force to the strike plate with a hammer or the like to drive the trial component into the bone. A similar process may be used with femoral trial components on the distal end of the femur.

Another instrument that may be used during a knee arthroplasty procedure is an extractor, which removes the trial components and other surgical instruments (e.g., cut blocks, broaches, etc.) from the bone to allow for implantation of the actual knee replacement components. A slap hammer is one type of extractor known in the art having a weight slidably coupled to a rod that connects to the implanted trial component. The surgeon may slide the weight along the rod until the weight contacts a stopper, thereby creating an impulse that dislodges the implanted trial component. Moreover, a slap hammer may be used during knee revision to facilitate removal of previously implanted knee replacement components. Knee revision surgery may be required when implanted components need to be removed due to injury, wear, infection, or if there were issues with the original knee arthroplasty. In any case, after the trial components or other previously implanted components are removed, the surgeon may insert the new knee replacement components via the impactor as stated above.

Typically, the suite of instruments delivered to the operating room to perform knee arthroplasty will have various impactors for positioning and implanting trial and final components and a slap hammer or multiple slap hammers to extract components that have been impacted into bone. The impactors and slap hammer(s) are generally located on surgical trays that include additional surgical equipment and/or component parts. Because different components require different impactors and/or slap hammers, the surgical trays may take up more space than desirable in an operating room. Furthermore, there are mass constraints on the surgical trays and therefore the use of multiple impactors and slap hammers can require additional surgical trays. This exacerbates the issue of instruments and trays crowding an otherwise space constrained operating room. Furthermore, there are substantial costs associated with sterilizing all of the impactors, slap hammers, surgical equipment, and knee replacement components. As such, convention still requires the use of multiple individual surgical instruments that increase the mass of surgical trays, number of surgical trays, and/or sterilization costs of knee arthroplasties.

There exists, therefore, a significant need in the art for a dual-purpose orthopedic surgery instrument usable as a modular impactor when used alone with an impactor head that selectively couples thereto and usable as a weight component of a slap hammer when selectively coupled along the length of an extractor in slidable relation relative thereto. The present invention fulfills these needs and provides further related advantages.

SUMMARY OF THE INVENTION

In general, the dual-purpose orthopedic surgery instrument disclosed herein serves as a modular impactor when used alone with an impactor head selectively coupled to an impactor interface of an impactor block opposite a strike block, and serves as a weight component of a slap hammer when an extractor rod selectively couples thereto in slidable relation therewith.

More specifically, in one embodiment, the dual-purpose orthopedic instrument as disclosed herein may include an elongated body, an impactor block formed from a first end of the elongated body selectively couplable with a modular impactor head, a strike block formed from a second end of the elongated body including a strike surface for selectively receiving a strike force thereon, and an externally accessible channel having a size and shape for pass-through reception and select retention of an extractor rod therein. As such, the elongated body is usable as a modular impactor when the impactor block is selectively coupled with the impactor head and as a weight of a slap hammer when selectively coupled with the extractor rod in slidable relation relative thereto.

In some embodiments, the first end may include a tapered channel having a size and shape for at least partial reception of a first end of the extractor rod at an angle offset from a longitudinal axis of the elongated body while at the same time a second end of the extractor rod may simultaneously extend out from the externally accessible channel. Moreover, the second end may include a receiving channel having a size and shape for tilt-in insertion of the second end of the extractor rod through the externally accessible channel. In this respect, at least a portion of the extractor rod may be keyed for insertion within the receiving channel in a predetermined orientation. To key the orientation of the extractor rod within the receiving channel, at least a portion of the extractor rod may include a pair of planar surfaces located along a length thereof positioned to abut a commensurate pair of interior planar surfaces of the receiving channel when the extractor rod is inserted therein. Here, the abutting planar surfaces prevent coaxial rotation of the extractor rod relative to the elongated body.

Upon full insertion of the extractor rod within the receiving channel, the extractor rod may reside substantially coaxial within the externally accessible channel and in slidable relation with within the elongated body. The extractor rod may further include a stopper relatively smaller than the externally accessible channel yet relatively larger than the tapered channel and the receiving channel for purposes of removably retaining the extractor rod within the elongated body between the first end and the second end after being tilted into engagement with the elongated body. Here, the extractor rod may be of a length at least partially residing within the first end when the stopper is seated within the tapered channel and at least partially residing within the second end when the stopper is in contact with the first end. The externally accessible channel may be in the form of an arcuate channel such that the stopper is relatively larger than an upper section and a lower section of the arcuate channel and relatively smaller than a middle section of the arcuate channel for pass-through reception therewith.

In another aspect of the embodiments disclosed herein, the impactor block may include a spring-actuated button at least partially residing within an internal enclosure of the strike block and generally biasing a lock in a normal closed position at least partially enclosing the receiving channel. Doing so may help prevent slide-out removal of the second end of the extractor rod from the elongated body. In one embodiment, the lock may include a chamfered latch self-actuable by the second end of the extractor rod, i.e., the extractor rod may simply slidably engage and displace the chamfered latch to open access to the receiving channel for receipt of the extractor rod therein.

In an alternative embodiment, the externally accessible channel may include a locking slot formed from a portion of one of the impactor block or the strike block. Here, a lever normally positioned within the externally accessible channel may generally block passthrough movement of the outwardly projecting stopper formed along a length of the extractor rod. An externally accessible button may be actuable to selectively displace the lever out from within the externally accessible channel, thereby permitting the outwardly projecting stopper to pass therethrough. When in this open position, the extractor rod may be selectively inserted and/or withdrawn from the elongated body.

In other embodiments as disclosed herein, the modular impactor head may include an aperture having a size and shape for pass-through reception of at least a portion of the extractor rod. Additionally, the strike surface may be an angled surface offset from a longitudinal axis of the elongated body, or the strike surface may be a non-planar strike surface selected from the group consisting of a curved surface, a spherical surface, and a spheroidal surface. Additionally, the elongated body may include a tab outwardly extending therefrom selectively couplable to an orthopedic component and the impactor block may include an impactor interface having a size and shape for select coupling to the impactor head via snap-fit engagement, threaded engagement, or slide-fit engagement.

In another embodiment, a slap hammer as disclosed herein may include a handle having an externally accessible channel wherein a first end of the handle includes a tapered channel formed therein and a second end of the handle includes a receiving channel formed therein. The slap hammer may further include an extractor rod having an outwardly extending stopper formed along a length thereof, wherein the stopper is of a size and shape relatively smaller than the externally accessible channel while being relatively larger than the tapered channel and the receiving channel. The extractor rod may be at least partially insertable into the tapered channel at an angle offset from a longitudinal axis of the handle and tiltable therein to pass the stopper through the relatively larger externally accessible channel for insertion of the extractor rod into the receiving channel in coaxial relation relative to the handle. Thereafter, the handle is movable along the length of the extractor rod as a weight of the slap hammer and remains constrained to the extractor rod by the stopper between the first end and the second end.

In these embodiments, the first end may include an impactor block selectively couplable with a modular impactor head and the second end may include a strike block having a strike surface for selectively receiving a strike force thereon. Moreover, the externally accessible channel may be an arcuate channel, wherein the stopper is relatively larger than an upper section and a lower section of the arcuate channel and relatively smaller than a middle section thereof. At least a portion of the extractor rod may be keyed for insertion within the receiving channel in a predetermined orientation. More specifically with respect to this feature, at least a portion of the extractor rod may include a pair of planar surfaces located along a length thereof positioned to abut a commensurate pair of interior planar surfaces of the receiving channel, the abutting planar surfaces thereby prevent coaxial rotational movement of the extractor rod relative to the elongated body. Additionally, the extractor rod may at least partially reside within the first end when the stopper is seated within the tapered channel and may at least partially reside within the second end when the stopper is in contact with the first end.

In another aspect of these embodiments, a button may generally bias a lock in a normal closed position at least partially enclosing the receiving channel thereby preventing slide-out removal of the extractor rod therefrom. Here, the lock may include a chamfered latch self-actuable by the extractor rod to facilitate push-in reception thereof without the need to actuate the button. The button may more specifically be spring-actuated and at least partially reside within an internal enclosure of the first end of the handle.

In another embodiment as disclosed herein, a process for extracting an orthopedic component with a dual-purpose orthopedic instrument may include steps for inserting an extractor rod into an externally accessible channel of a weight at an angle offset from a longitudinal axis thereof, tilting the extractor rod into the externally accessible channel until the extractor rod is generally coaxially aligned within the weight, attaching the extractor rod to an orthopedic component, sliding the weight along at least a portion of the extractor rod, and creating an impulse sufficient to extract the orthopedic component.

More specifically, the creating step may include impacting the weight against an outwardly extending collar formed along a length of the extractor rod to generate the extracting impulse. Here, the collar may be of a size and shape to permit passing the collar through the externally accessible channel as part of the tilting step. Once the extractor rod is engaged with the handle, the extractor rod may be constrained therein by way of the collar being positioned between an impactor block formed from a first end of the weight and a strike block formed from a second end of the weight. As such, the sliding step may further include passing at least a portion of the extractor rod through a tapered channel formed through the impactor block and a receiving channel formed through the strike block, both the tapered channel and the receiving channel being of a size and shape relatively smaller than the collar to stop sliding movement of the extractor rod therein when coming into contact with the collar.

Moreover, the tilting step may further include orienting the extractor rod in a predetermined orientation keyed for reception within a receiving channel, including passing the extractor rod over a chamfered latch of a self-actuable lock for locking engagement therein once the extractor rod clears the chamfered latch. To remove, an externally accessible button may be pressed to operably open the self-actuable lock, thereby allowing the extractor rod to be tilted out from engagement with the weight.

In accordance with another embodiment disclosed herein, the dual-purpose orthopedic surgery instrument may include an elongated handle terminating in an impactor block having an impactor interface that may selectively couple to at least one modular impactor head at one end and a strike block at another end thereof. The elongated handle may further include one or more elongated channels starting at the strike block and generally extending along the length of the elongated handle and terminating at the impactor block.

In another embodiment, the elongated handle may be ergonomically shaped and the modular impactor interface may include a recess for selectively coupling to at least one modular impactor head via snap-fit or slide-fit engagement. Alternatively, the impactor interface may selectively couple an impactor head via threaded engagement. In another embodiment, the strike block may include a flat or curved strike surface, wherein the curved strike surface may include a spherical surface or a spheroidal surface. In another embodiment, the strike surface may be angled relative to the longitudinal axis of the dual-purpose orthopedic surgery instrument. The strike block may further include a keyed rod-receiving channel for retaining an extractor rod to form a slap hammer when coupled thereto. A spring-loaded button housed within an enclosure of the strike block may help retain the extractor head within the dual-purpose orthopedic surgery instrument. In one embodiment, the spring-loaded button may have an externally accessible corrugated tab and be biased into a normal engaged position by a latch. The spring-loaded button may be selectively pressed into an open position aligning the spring-loaded button opening with the keyed rod-receiving channel, and released into a closed position wherein the spring-loaded button latch extends into the elongated handle channel to hook the extractor rod therein.

In another embodiment, an extractor rod may be inserted into and extend through the elongated channel, wherein the extractor rod may be removably constrained therein. Here, the elongated handle may couple to the extractor rod in slidable relation relative thereto, thereby allowing the dual-purpose orthopedic surgery instrument to be used as a slap hammer. Of course, the dual-purpose orthopedic surgery instrument can still be used as a modular impactor when the rod is removed from the handle. The extractor rod may include a tibial extractor coupled to one end and a femoral extractor coupled to the other. Alternatively, the ends of the extractor rod may be adapted to couple to tibial trials, femoral trials, insert trials, implant components, or intramedullary rods. The extractor rod may also include a stopper with a width small enough to fit within the elongated channel but large enough to prevent the extractor rod from completely sliding off of the strike block and the impactor block. In another embodiment, extractor rod may be prevented from disassembly with the elongated handle via the spring-loaded button and latch while the device is used as an extractor or slap hammer. The extractor rod may have a keyed-cross section, such as two opposing flat sides and two opposing rounded sides. Alternatively, the extractor rod, the elongated channel, and the stopper may have a cross-section that is circular, square, or triangular to facilitate keyed engagement. The extractor rod may couple to tibial trials, femoral trials, insert trials, implant components, or intramedullary rods via snap-fit coupling, slide-fit coupling, or threaded coupling. In yet another embodiment, the stopper and the extractor rod may be of a unibody construction, or may be two separately formed pieces that couple together. The impactor block may also include a tab for positioning a tibial insert.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
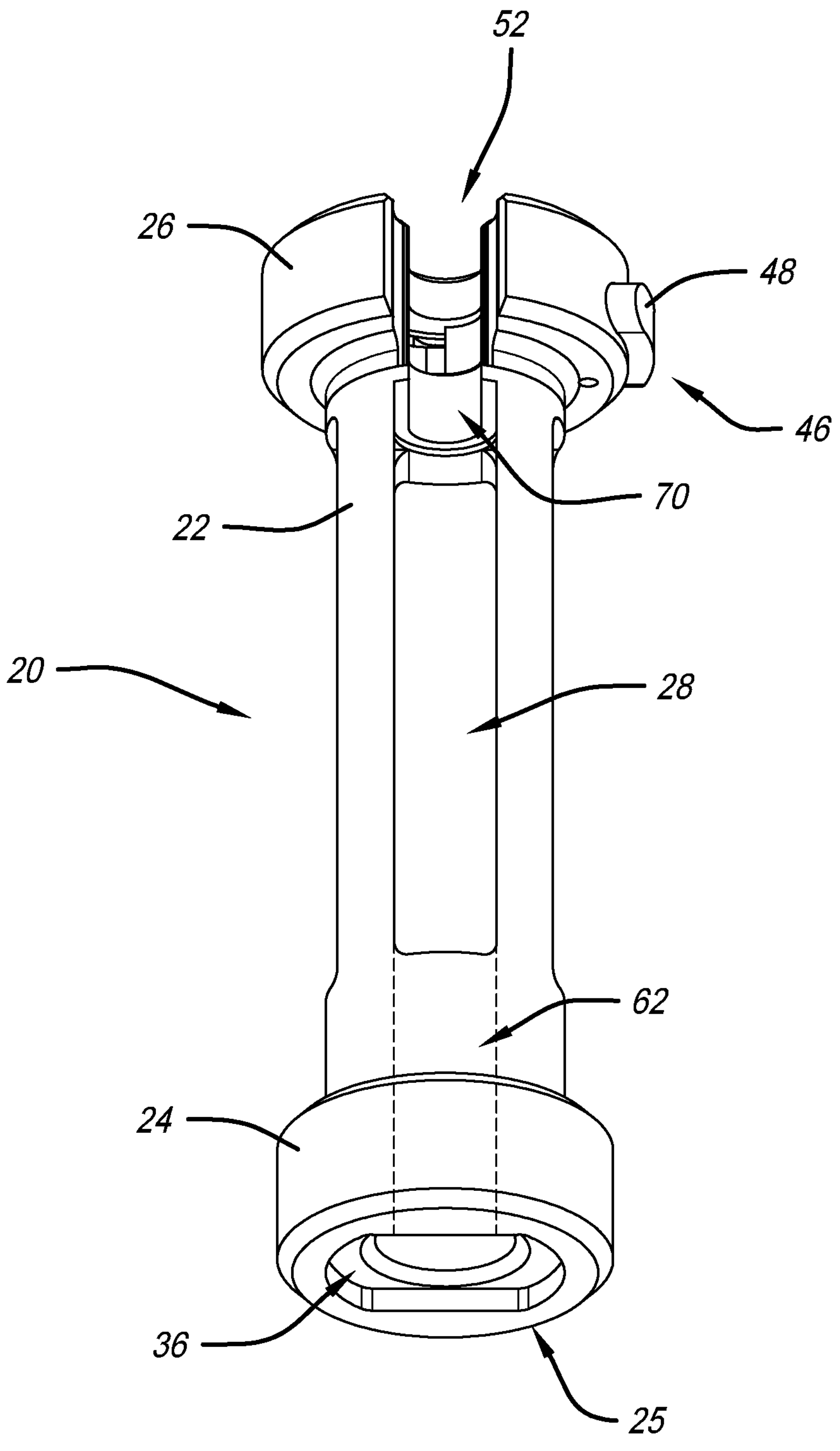
FIG. 1 is a perspective view of a dual-purpose orthopedic surgery instrument as disclosed herein.

As shown in the exemplary drawings for purposes of illustration, the present invention for a dual-purpose orthopedic surgery instrument is generally illustrated in FIGS. 1-3, 6-8, 10-12, and 14-16 and 18 with respect to reference numeral 20. In general, the dual-purpose orthopedic surgery instrument 20 may include an elongated handle 22 terminating in an impactor block 24 having an impactor interface 25 at one end and a strike block 26 at another end thereof. The elongated handle 22 may be ergonomically formed (e.g., in an oval or bulbous configuration suitable for gripping) that includes at least one elongated channel 28 formed therein to at least facilitate slide-in engagement of an extractor rod 30 (FIGS. 5-6, 8, 10, 12-14, 16, and 18), wherein the combination forms a slap hammer 32 as discussed in more detail below. In this respect, the dual-purpose orthopedic surgery instrument 20 can operate as an impactor instrument when used alone with a modular impactor head 34 coupled to the impactor interface 25 (FIG. 2), and also as a slide weight as part of the slap hammer 32, e.g., as illustrated in FIGS. 6, 12, 16, and 18. Accordingly, such versatility of the dual-purpose orthopedic surgery instrument 20, including by way of the fact that the impactor interface 25 may couple to different modular impactor heads 34 of various sizes and configurations, the number of surgical instruments required in the operating room can be significantly reduced.

More specifically, in one use, a surgeon may use the dual-purpose orthopedic surgery instrument 20 as a modular impactor by selectively coupling the modular impactor head 34 to the impactor interface 25 of the impactor block 24. In one embodiment, the impactor block 24 may include a recess 36 that facilitates snap-fit engagement with the modular impactor head 34. Here, the modular impactor head 34 may have a protrusion (not shown) that mates with the recess 36 by extending into the recess 36. For example, the protrusion may have a groove containing an O-ring configured to mate with a lip in the recess 36. The lip may extend into the groove containing the O-ring thereby facilitating snap-fit coupling between the modular impactor head 34 and impactor interface 25. In alternative embodiments, the modular impactor head 34 may couple to the recess 36 and/or the impactor interface 25 via a threaded coupling. Here, the recess 36 may include a set of internal threads and the modular impactor head 34 may include a set of external threads of a size and shape to engage the internal threads of the recess 36 such that the modular impactor head 34 can screw on to the dual-purpose orthopedic surgery instrument 20 in thread-tight relationship. In another embodiment, the impactor interface 25 may include a channel extending to the peripheral edge thereof and the modular impactor head 34 may couple thereto by sliding into said channel in the impactor interface 25. Although, of course, the modular impactor head 34 may couple to the impactor interface 25 by other methods known in the art for securing components adjacent to one another.

Figure 2:
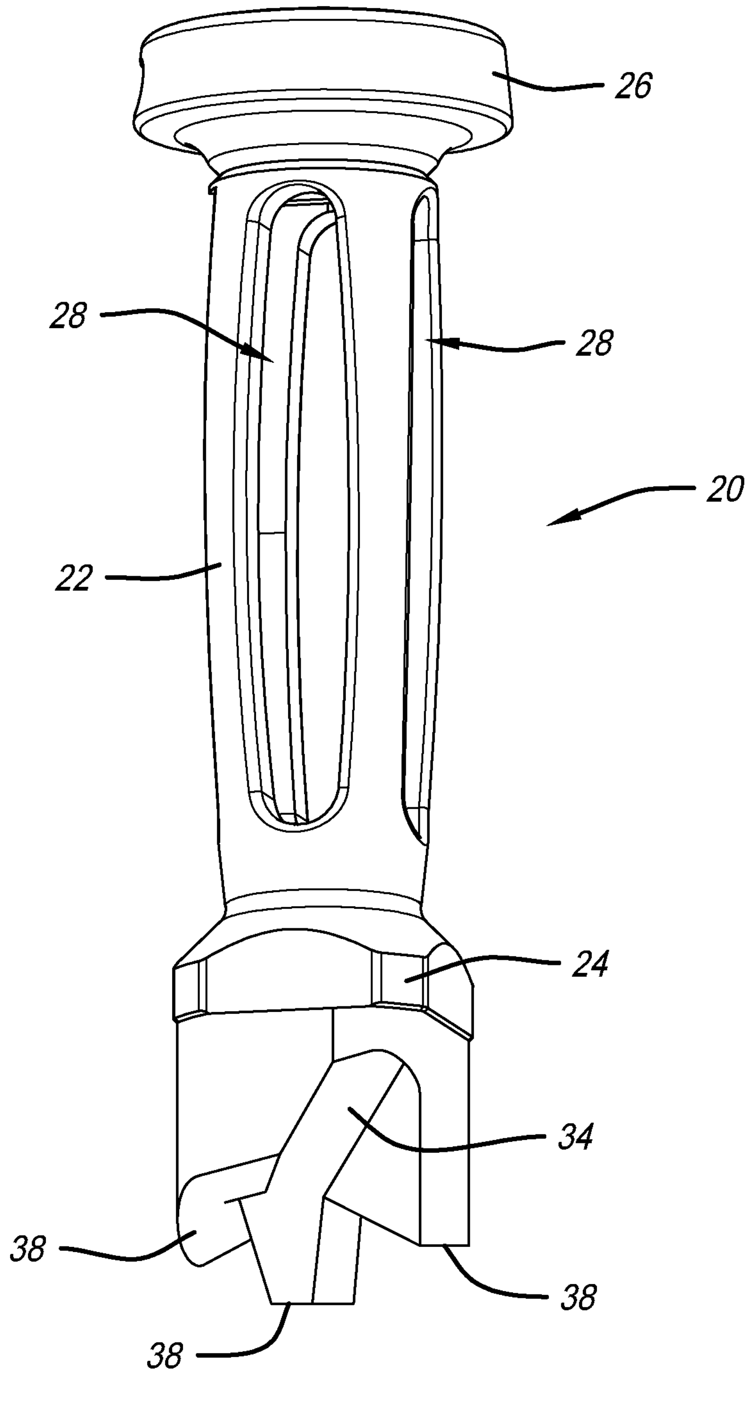
FIG. 2 is a perspective view of the dual-purpose orthopedic surgery instrument of FIG. 1, further illustrating a modular impactor head coupled to an impactor interface opposite a strike block.

The modular impactor head 34 illustrated in FIG. 2 includes a set of projections 38 (three) that may correspond to three indents or recesses formed in a knee replacement trial or component (not shown). Alternatively, the modular impactor head 34 may include fewer than three of the projections 38 (e.g., one or two of the projections 38) or more than the three projections 38. Conversely, the modular impactor head 34 may include a plurality of indentations that correspond to a plurality of protrusions projecting out from the knee replacement trial or component. In another alternative embodiment, the modular impactor 34 may be substantially flat (i.e., including none of the projections 38). Of course, any impactor head known in that art able to couple to or otherwise adapt for use with the impactor interface 25 may be used. Once the modular impactor head 34 is coupled to the impactor interface 25, the surgeon may position the modular impactor head 34 on a trial or implant component surface for use of the dual-purpose orthopedic surgery instrument 20 as an impactor.

Figure 3:
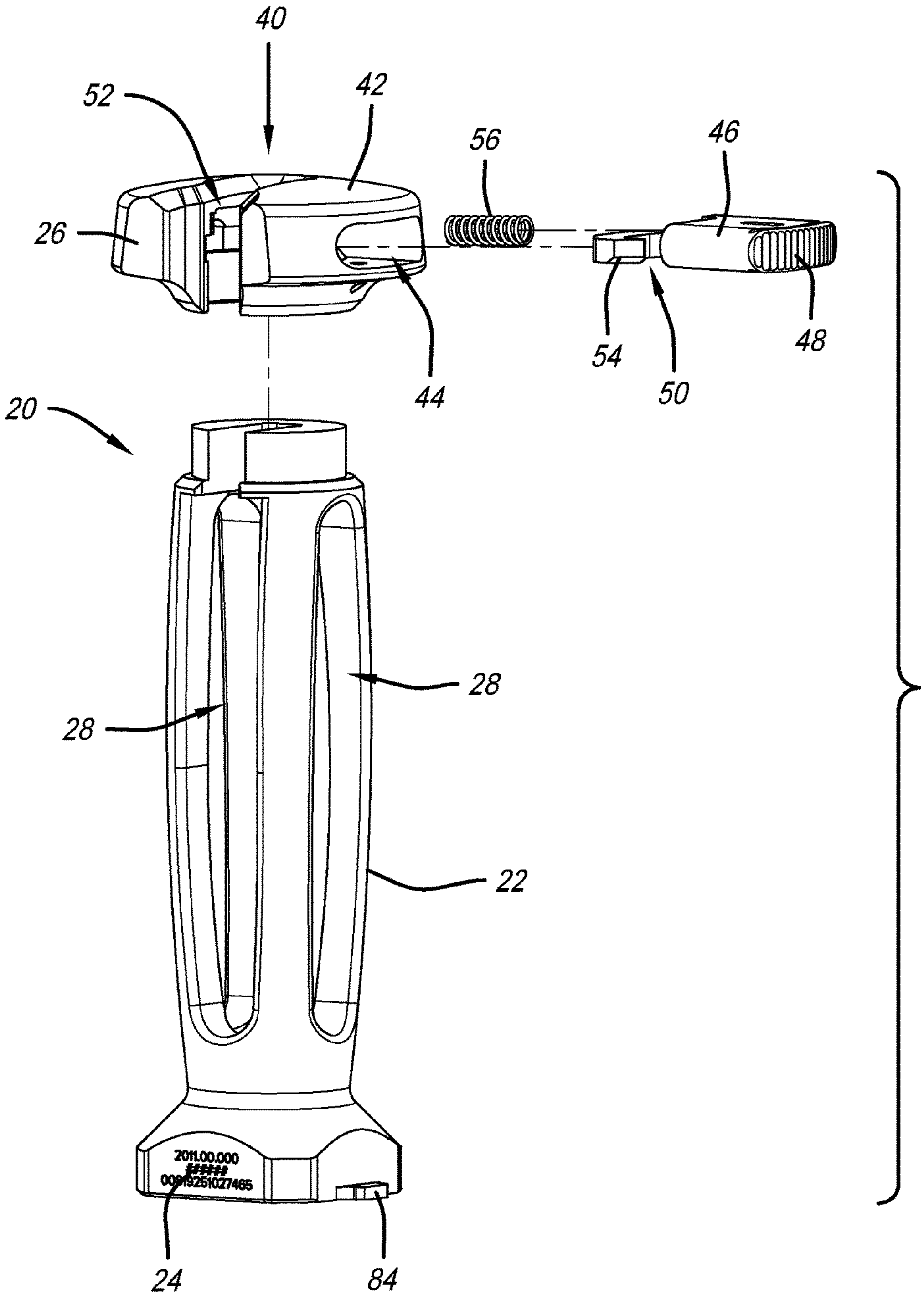
FIG. 3 is a perspective view of the dual-purpose orthopedic surgery instrument, further illustrating a spring-activated button in exploded relation relative to a recess in the strike block.

In general, as best illustrated in FIG. 3, the surgeon may apply a strike force along an arrow 40 to a strike surface 42 of the strike block 26, e.g., by way of a hammer or the like during surgery, to impact a trial or implant component into a patient bone (e.g., the proximal end of a tibia and/or distal end of a femur). The strike surface 42 may be a substantially flat surface best shown in FIGS. 8, 13 and 16-18, or the strike surface 42 may include a non-planar surface such as a curved, spherical, or spheroidal surface. The strike block 26 and the strike surface 42 may also be generally parallel to the impactor block 24, or the strike surface 42 may formed as an angled strike surface angularly offset from a longitudinal axis of the impactor block 24 where the modular impactor head 34 is couples to the impactor interface 25.

Figure 4:
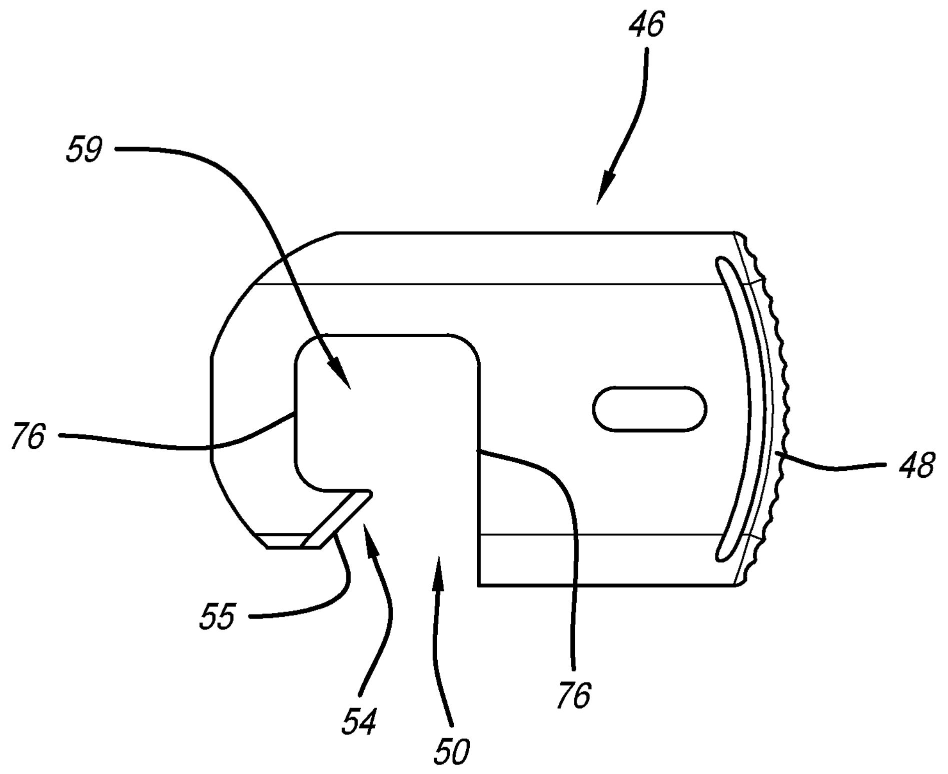
FIG. 4 is a top plan view of the spring-activated button, further illustrating a cavity formed therein for selectively receiving and retaining an extractor rod therein.
Figure 5:
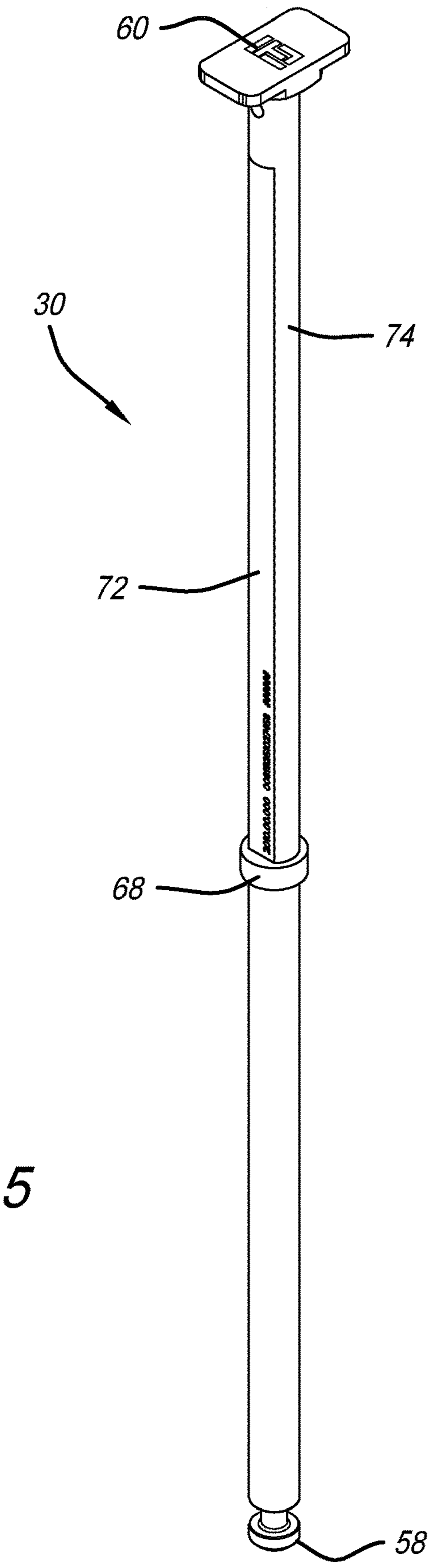
FIG. 5 is a perspective view of an extractor rod having a keyed cross-section selectively engageable with the keyed rod-receiving channel of the dual-purpose orthopedic surgery instrument.
Figure 13:
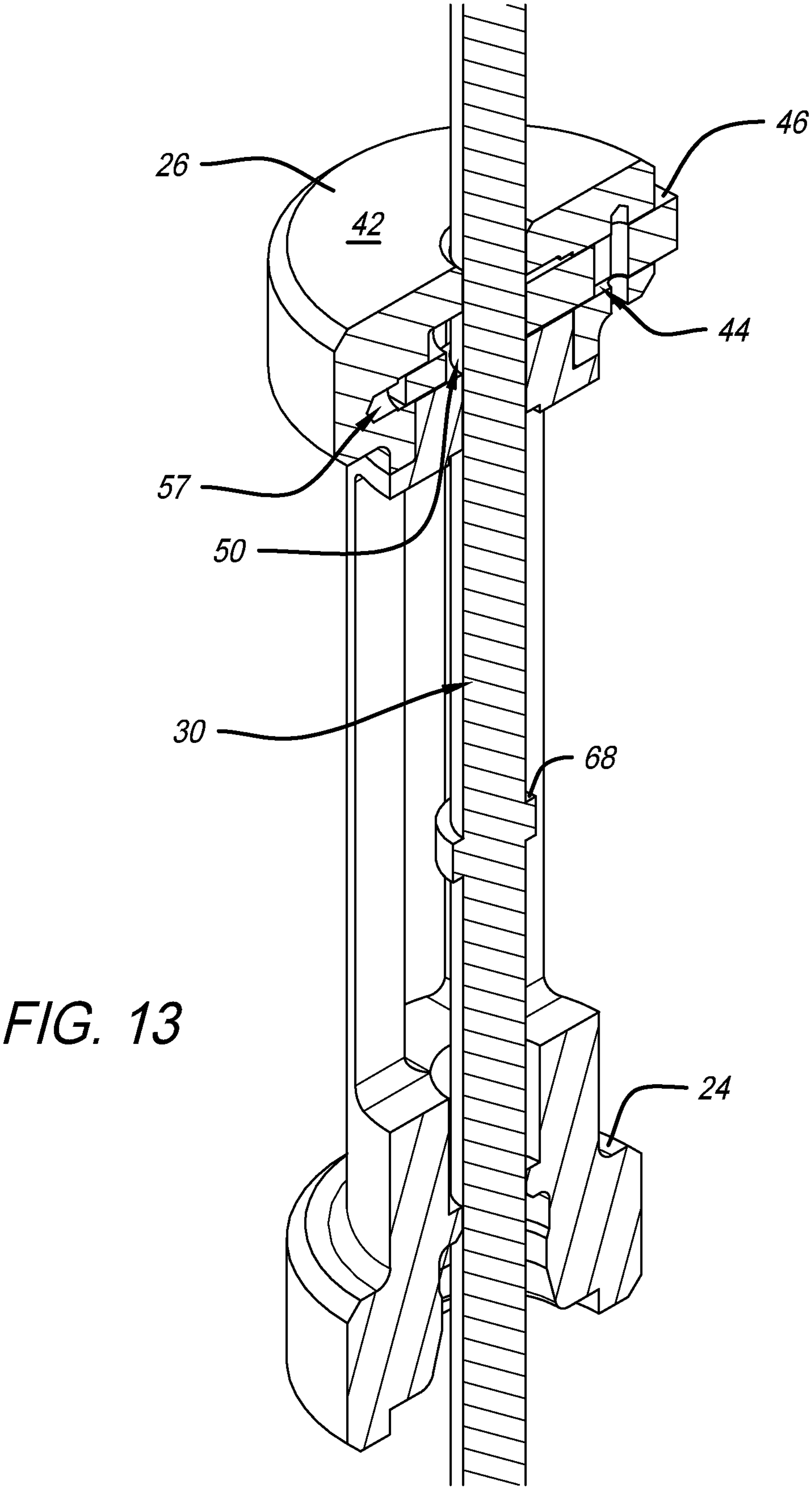
FIG. 13 is an enlarged cross-sectional view taken about the line 14-14 in FIG. 8, further illustrating an internal enclosure housing a spring-loaded latch in the strike block.
Figure 14:
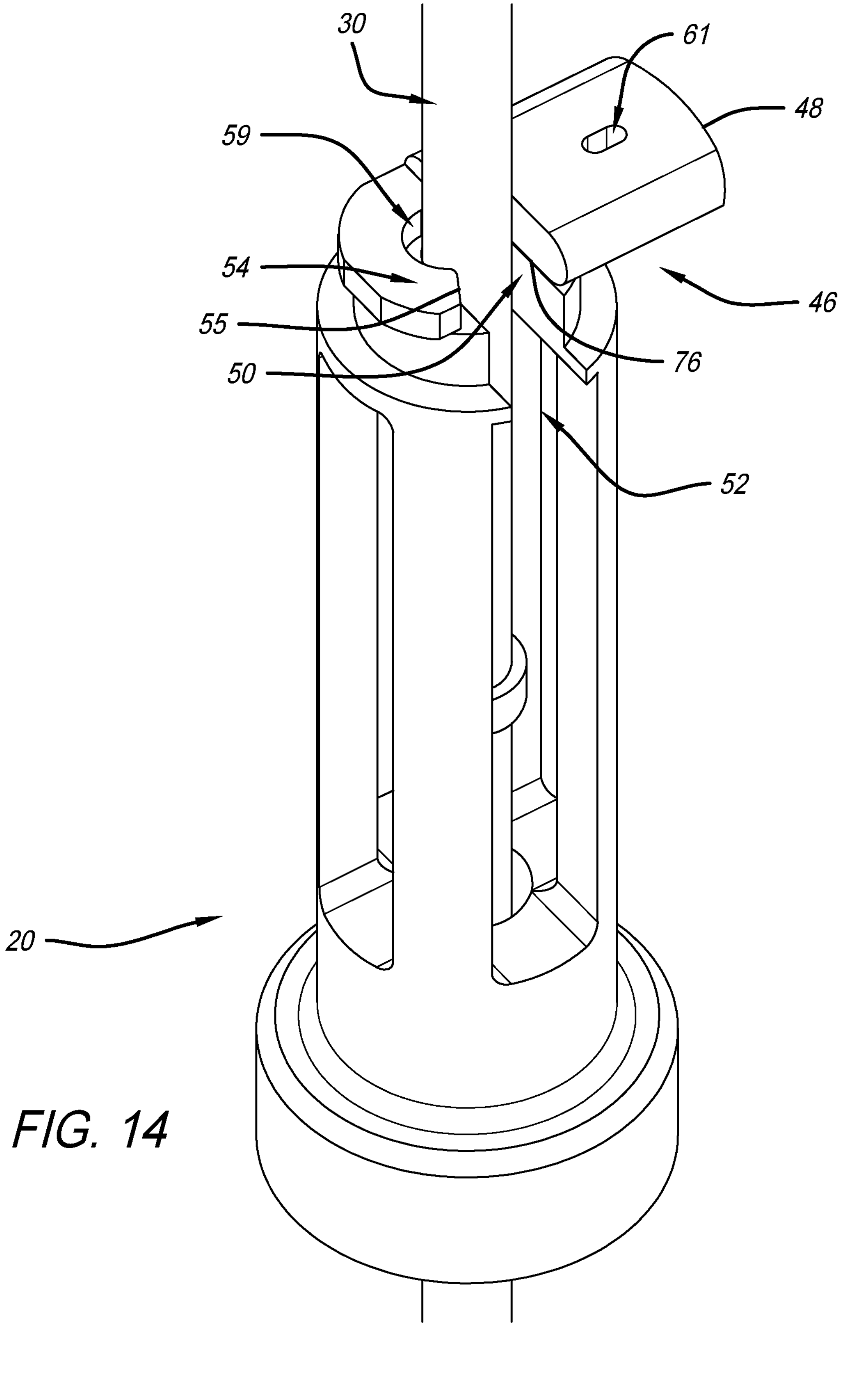
FIG. 14 is an enlarged perspective view similar to FIG. 8 omitting the strike plate to further illustrate the positioning of the latch relative to the extractor rod when the spring-loaded button is in a depressed position.
Figure 15:
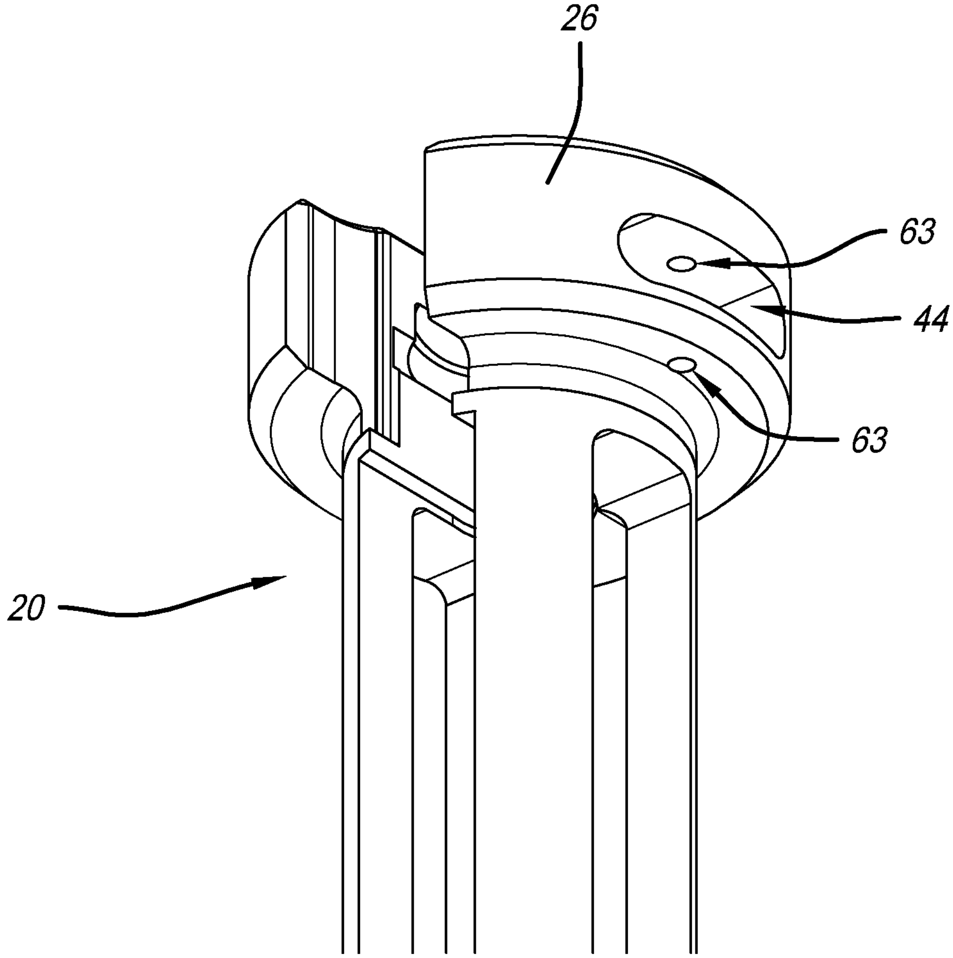
FIG. 15 is an alternative enlarged bottom perspective view similar to FIGS. 8 and 14 omitting the spring-loaded button to illustrate a pair of pin retaining apertures formed in the strike block.

As further illustrated in FIGS. 3, 13 and 15, the strike block 26 may also have an enclosure 44 housing a spring-loaded button 46. As best illustrated in FIGS. 4 and 14, the spring-loaded button 46 has a disk-shaped configuration conducive for sliding back-and-forth within the enclosure 44 between locked and unlocked positions. Specifically in this respect, the spring-loaded button 46 has planar shape that generally tracks the size and shape of the strike block 26, albeit an externally accessible corrugated tab 48 designed to enhance fictional engagement during hand depressed operation thereof may extend out from one side thereof as illustrated, e.g., in FIGS. 6, 8, and 13. Moreover, to an interior thereof, the spring-loaded button 46 may further include an opening 50 formed opposite the corrugated tab 48 that generally tracks the size and shape of a keyed rod-receiving channel 52 therein when the spring-loaded button 46 is depressed within the enclosure 44. Doing so allows insertion of the extractor rod 30, as discussed in more detail below. One side of the opening 50 may further include an inwardly projecting latch 54 having a chamfer 55 that forms an inwardly extending ramp that facilitates slide-in reception of the extractor rod 30 into the opening 50 for retainment therein by the spring-loaded button 46.

When in a normal non-use or undepressed position, a spring 56 (FIG. 56) residing in a spring retaining chamber 57 in the strike block 26 (FIG. 13) generally biases the spring-loaded button 46 in a position wherein the latch 54 at least partially resides within the keyed rod-receiving channel 52 and the inwardly extending chamfer 55 at least partially encompasses the extractor rod 30 to prevent return travel out from the keyed rod-receiving channel 52 when the extractor rod 30 is mounted or otherwise engaged with the dual-purpose orthopedic surgery instrument 20. Also, when in this position, the corrugated tab 48 generally projects out from a side of the strike block 26 for relatively easy engagement and depression thereof. Depressing the spring-loaded button 46 against the internally located spring 56 displaces the latch 54 out from a blocking relationship within the keyed rod-receiving channel 52 to permit movement of the extractor rod 30 out from the dual-purpose orthopedic surgery instrument 20. That is, when the spring 56 is compressed, the opening 50 in the spring-loaded button

46 may generally align with the keyed rod-receiving channel 52 thereby permitting the extractor rod 30 to be removed therefrom.

Insertion may simply involve pushing the extractor rod 30 into the keyed rod-receiving channel 52 and into engagement with the chamfer 55 residing therein. So long as the insertion force is greater than the extension force exerted by the spring 56, the extractor rod 30 will travel down along the incline of the chamber 55, thereby causing the spring-loaded button 46 to place a compressive force on the spring 56. The spring-loaded button 46 is able to move side-to-side within the enclosure 44 to displace the latch 54 by a distance sufficient to allow the extractor rod 30 to pass through the opening 50 and into a cavity 59. Once the extractor rod 30 reaches the cavity 59 and is no longer in engagement along the incline of the chamfer 55, the spring 56 is allowed to expand outwardly to relocate the spring-loaded button 46 in the enclosure 44 to a normal closed or locked position whereby the latch 54 at least partially extends out and around the extractor rod 30 to retain the extractor rod 30 within the keyed rod-receiving channel 52. The extractor rod 30 will remain therein until the external corrugated button 48 is depressed inwardly again compressing the spring 56 within the spring retaining chamber 57 to displace the latch 54 out from generally encompassing the extractor rod 30. The spring-loaded button 46 may include a slide channel 61 (FIG. 14) having a width sufficient to allow said side-to-side movement of the spring-loaded button 46 within the enclosure 44 to enable the latch 54 to selectively lock and/or unlock the extractor rod 30 within the keyed rod-receiving channel 52. The strike block 26 may include a pair of coaxially aligned pin retaining apertures 63 that selectively receive a pin therein (not shown) that extends through the slide channel 61 aligned therewith. As such, the pin will only permit the spring-loaded button 46 to move side-to-side in the enclosure 44 a distance approximately that of the width of the slide channel 61 as a result.

In an alternative embodiment, the spring-loaded button 46 may include a locking feature similar to that of a pen that retains the spring-loaded button 46 in an open position where the opening 50 remains substantially aligned with the keyed rod-receiving channel 52 when moved a sufficient distance within the enclosure 44. Here, the spring 56 remains continually depressed without the need to continually depress the spring-loaded button 46. Pressing the spring-loaded button 46 a second time may disengage or unlock the spring-loaded button 46 so that the spring 56 may bias the spring-loaded button 46 back to the closed position where the latch 54 is able to encompass the extractor rod 30 if in the keyed rod-receiving channel 52. The process can be repeated depending on whether the extractor rod 30 is to be inserted or removed from the keyed rod-receiving channel 52. Alternatively, insertion of the extractor rod 30 may require that the surgeon continuously depress the spring-loaded button 46 to maintain the opening 50 in an aligned position with the keyed rod-receiving channel 52.

In one embodiment, the extractor rod 30 may include additional couplings for purposes of being adapted to extract trial components, actual implant components, intramedullary rods, and/or inserts. For instance, the extractor rod 30 may include a tibial extractor 58 formed from one end thereof and a femoral extractor 60 formed from an opposite end thereof.

Figure 6:
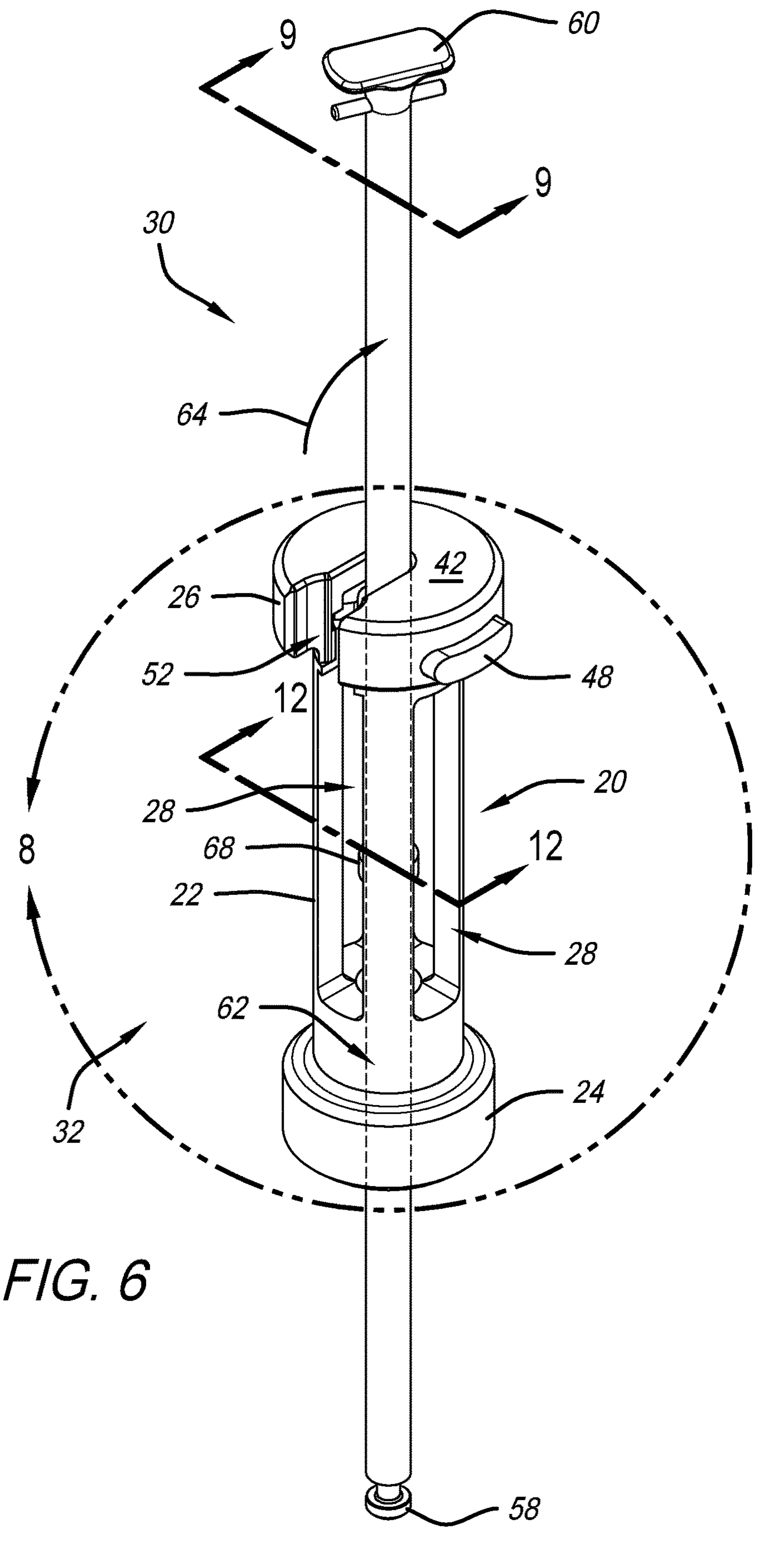
FIG. 6 is a perspective view illustrating engagement of the dual-purpose orthopedic surgery instrument along a length of the extractor rod.
Figure 7:
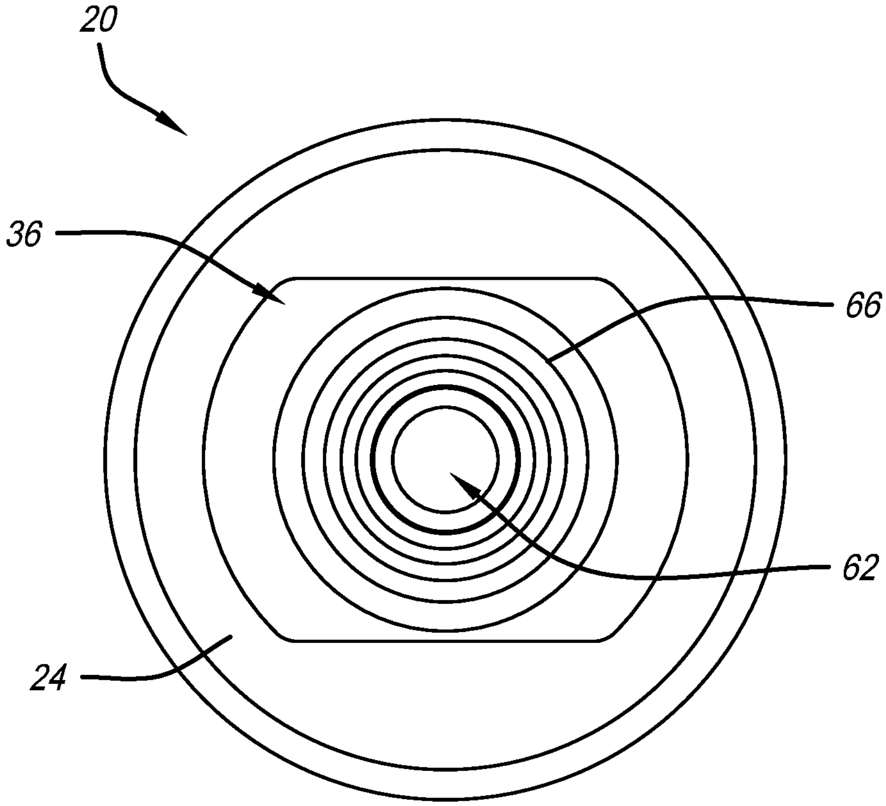
FIG. 7 is a bottom plan view of the dual-purpose orthopedic surgery instrument, further illustrating a bottom channel and recess formed longitudinally through the handle having a tapered inner wall at the modular impactor interface.
Figure 12:
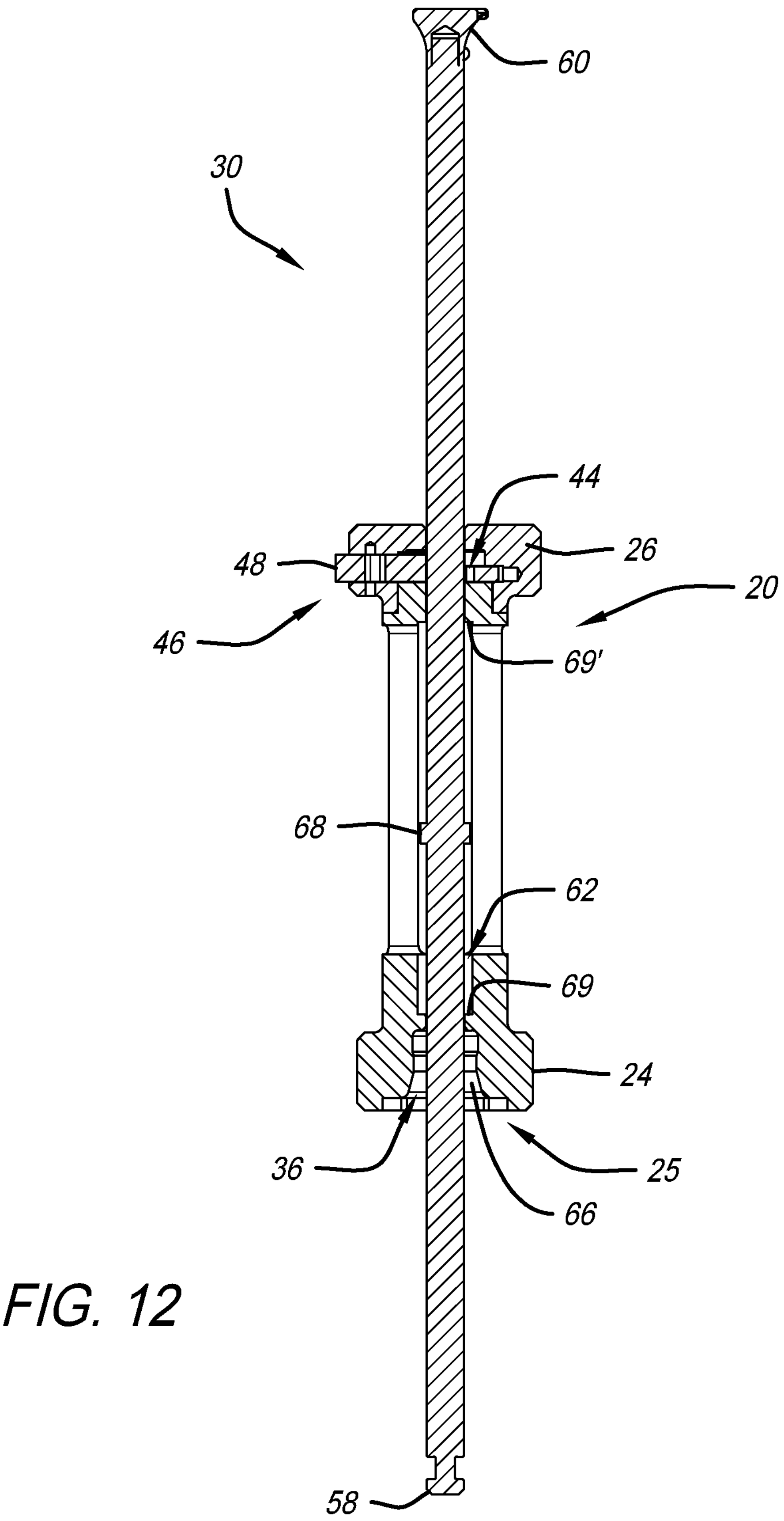
FIG. 12 is cross-sectional view taken about the line 12-12 in FIG. 6, further illustrating relative sizing of the stopper to each of a first shoulder in the impactor block and a second shoulder in the strike block.

To form the slap hammer 32 by way of engaging the dual-purpose orthopedic surgery instrument 20 with the extractor rod 30, the surgeon may first insert the tibial extractor 58 in through the elongated channel 28 in the dual-purpose orthopedic surgery instrument 20 and into a bottom channel 62 therein and eventually out through the impactor block 24 by way of the open recess 36 positioned below the bottom channel 62 as illustrated best in the cross-sectional view of FIG. 12. Initially, the extractor rod 30 may extend into each of the elongated channel 28 and the bottom channel 62 at an angle, whereby the upper portion of the extractor rod 30 having the femoral extractor 60 formed therewith must be rocked into engagement with the dual-purpose orthopedic surgery instrument 20 along an arrow 64 illustrated in FIG. 6. This causes the extractor rod 30 to slide into the keyed rod-receiving channel 52, thereby displacing the spring-loaded button 46 to permit insertion therein. As illustrated in FIG. 7, the recess 36 may include a tapered inner wall 66 having a relatively narrower opening near where the tibial extractor 58 is inserted therein (e.g., immediately below the bottom channel 62) after insertion through one of the elongated channels 28. As such, the tapered inner wall 66 provides additional tolerance out through the bottom of the impactor block 24 for the surgeon to at least somewhat axially displace the extractor rod 30 for purposes of insertion and removal. Once the extractor rod 30 is fully inserted, the spring-loaded button 46 moves within the enclosure 44 back to the normal closed position whereby the latch 54 retains the extractor rod 30 in position and prevents the extractor rod 30 from moving back into the keyed rod receiving channel 52.

Once inserted, the extractor rod 30 is removably constrained between the impactor block 24 and the strike block 26. Here, the dual-purpose orthopedic surgery instrument 20 is in slidable relation relative to the extractor rod 30. As illustrated in FIG. 6, the femoral extractor 60 is generally positioned above the strike block 26 and the tibial extractor 58 is generally positioned below the impactor block 24. In one embodiment, the modular impactor head 34 may include an aperture that aligns with the bottom channel 62 and the recess 36 thereby allowing the surgeon to insert the extractor rod 30 into the dual-purpose orthopedic surgery instrument 20 without decoupling the modular impactor head 34 from the impactor block 24.

Figure 8:
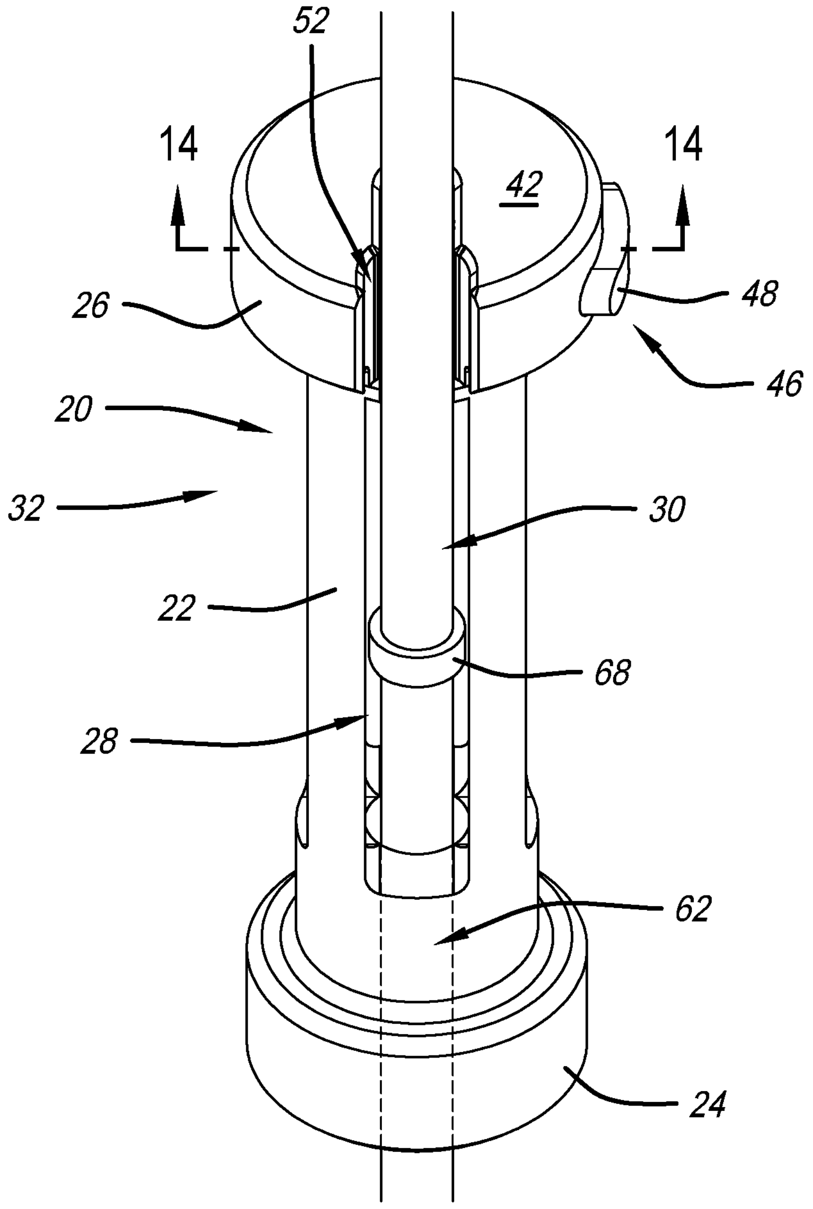
FIG. 8 is an enlarged perspective view taken about the circle 8 in FIG. 6, further illustrating a stopper outwardly extending from the extractor rod and located within a slide channel of the dual-purpose orthopedic surgery instrument.

As illustrated in FIG. 8, the extractor rod 30 may further include a generally circumferential stopper 68 outwardly extending about a portion of the extractor rod 30 to form a step or shoulder thereon. The stopper 68 is of a size and shape relatively smaller than the elongated channel 28 to permit slide through reception therein when engaging the extractor rod 30 with the dual-purpose orthopedic surgery instrument, yet of a size and shape relatively larger than the smallest diameter of the impactor block 24 and the strike block 26. For example, as best illustrated in the cross-sectional view of FIG. 12, each of the impactor block 24 and the strike block 26 include a respective set of inwardly projecting shoulders 69, 69' having an internal diameter relatively smaller than the outwardly projecting stopper 68, thereby preventing the dual-purpose orthopedic surgery instrument 20 from sliding off the extractor rod 30. As such, the surgeon can forcibly slide the dual-purpose orthopedic surgery instrument 20 along the length of the extractor rod 30 between each of the shoulders 69, 69' for purposes of using the device as the slap hammer 32 when the stopper 68 contacts one of the respective shoulders 69, 69'.

In an alternative embodiment, the elongated channel 28 may be wider near the middle of the elongated handle 22 and narrower toward the ends thereof, whereby the stopper 68 may be small enough to fit within the relatively wide portion of the elongated channel 28 but not through the narrower portions closer to each of the impactor block 24 and the strike block 26. The stopper 68 may be integrally formed with the extractor rod 30, or selectively coupled thereto as a separate component. For example, in an embodiment wherein the stopper 68 and extractor rod 30 are metal, the stopper 68 may be welded to the extractor rod 30.

Figure 9:
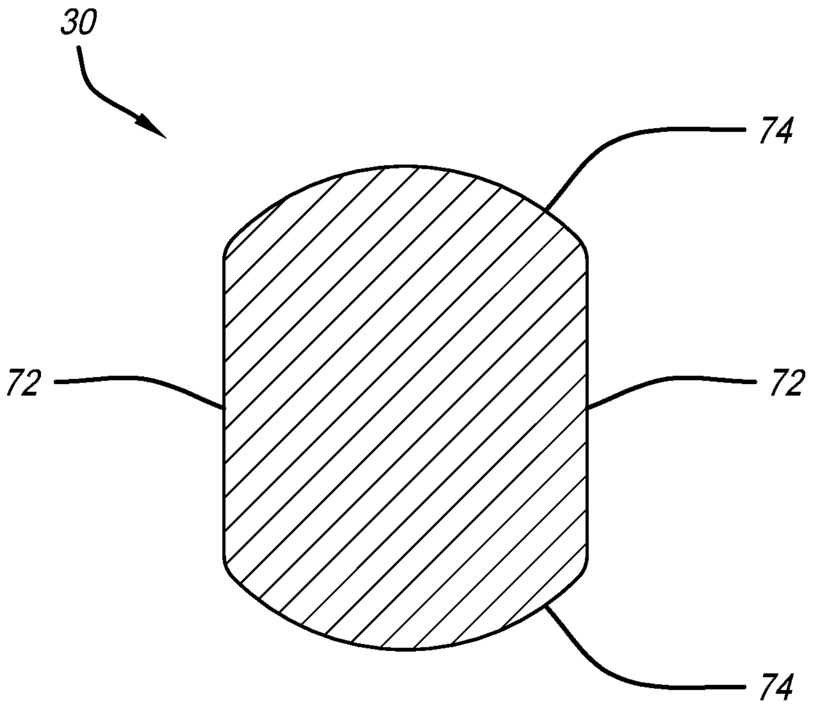
FIG. 9 is a cross-sectional view of the extractor rod taken about the line 9-9 in FIG. 6.

As illustrated in FIG. 9, the extractor rod 30 may have a keyed cross-section, such as a pair of flat sides 72 and a pair of rounded sides 74. In this respect, the width of the extractor rod 30 between each of the flat sides 72 may be somewhat relatively smaller than the opening formed by the keyed rod-receiving channel 52 to permit slide through engagement therewith. Moreover, the width of the extractor rod 30 between each of the rounded sides 74 may be relatively wider than the keyed rod-receiving channel 52 to prevent insertion therethrough. This helps ensure that the extractor rod 30 engages with the dual-purpose orthopedic surgery instrument 20 in the correct or desired orientation. Moreover, after insertion, the pair of flat sides 72 sit flush against a pair of inner flat surfaces 76 (FIG. 4) within the cavity 59 to prevent rotation of the extractor rod 30 relative to the dual-purpose orthopedic surgery instrument 20 during use. As such, this additional feature provides added stability during use of the dual-purpose orthopedic surgery instrument 20 as the slap hammer 32. The keyed cross section illustrated in FIG. 9 may extend substantially along the length of the extractor rod 30, or along certain sections thereof (e.g., near where the elongated extractor rod 30 would insert through the keyed rod receiving channel 52 into the spring-loaded button 46). In alternative embodiments, the extractor rod 30, bottom channel 62, and/or stopper 68 may have cross sections that are circular, square, triangular, or other shapes known in the art.

Figure 10:
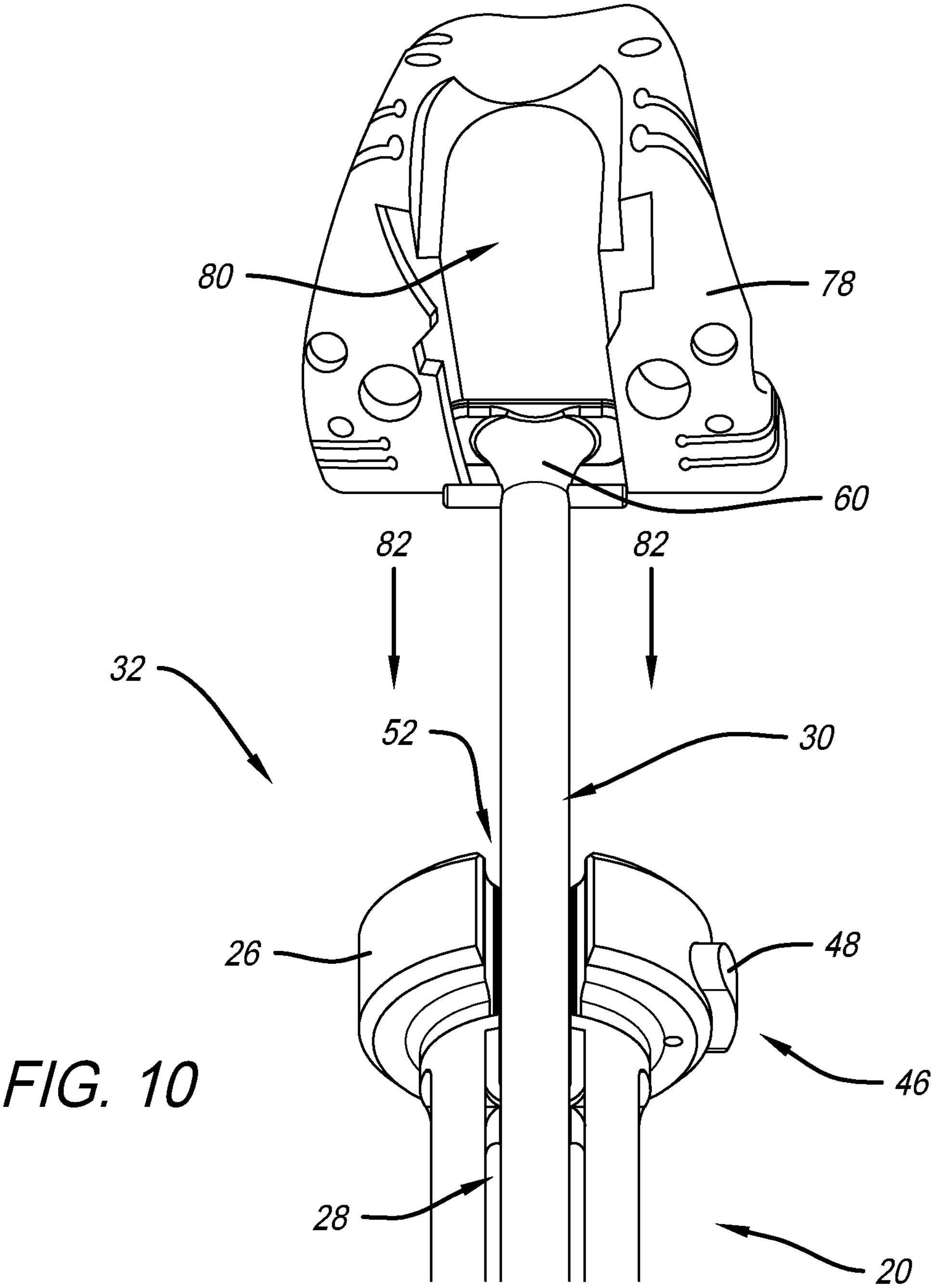
FIG. 10 is a perspective view illustrating a femoral trial interface engaged with a femoral trial component.

FIG. 10 illustrates another example wherein a surgeon may couple the femoral extractor 60 to a femoral trial 78 via a slot 80 therein. The surgeon may then slide the dual-purpose orthopedic surgery instrument 20 along the extractor rod 30 away from the femoral trial 78, such as along the direction indicated by arrows 82. The dual-purpose orthopedic surgery instrument 20 may slide along the extractor rod 30 until the shoulder 69' of the strike block 26 contacts the stopper 68. The force applied by the dual-purpose orthopedic surgery instrument 20 contacting the stopper 68 may create an impulse along the length of the extractor rod 30 that transfers to the femoral trial 78, thereby pulling the femoral trial 78 in the same direction as the arrows 82. The surgeon may repeat the process of sliding the dual-purpose orthopedic surgery instrument 20 away from the femoral trial 78, as is known in the art for the use of a slap hammer, until the femoral trial 78 is extracted from the distal end of a patient femur. Of course, a similar process may be performed with the tibial extractor 58 coupled to a tibial trial to extract the tibial trial from the proximal end of a patient tibia. In alternate embodiments, either end of the extractor rod 30 may couple to insert trials, tibial components, femoral components, intramedullary rods, cut blocks, broaches, or any other implant component and/or surgical instrument known in the art. The tibial extractor 58 and/or the femoral extractor 60 may couple thereto via snap-fit coupling, slide-fit coupling, threaded coupling, or any other method of coupling known in the art.

Figure 11:
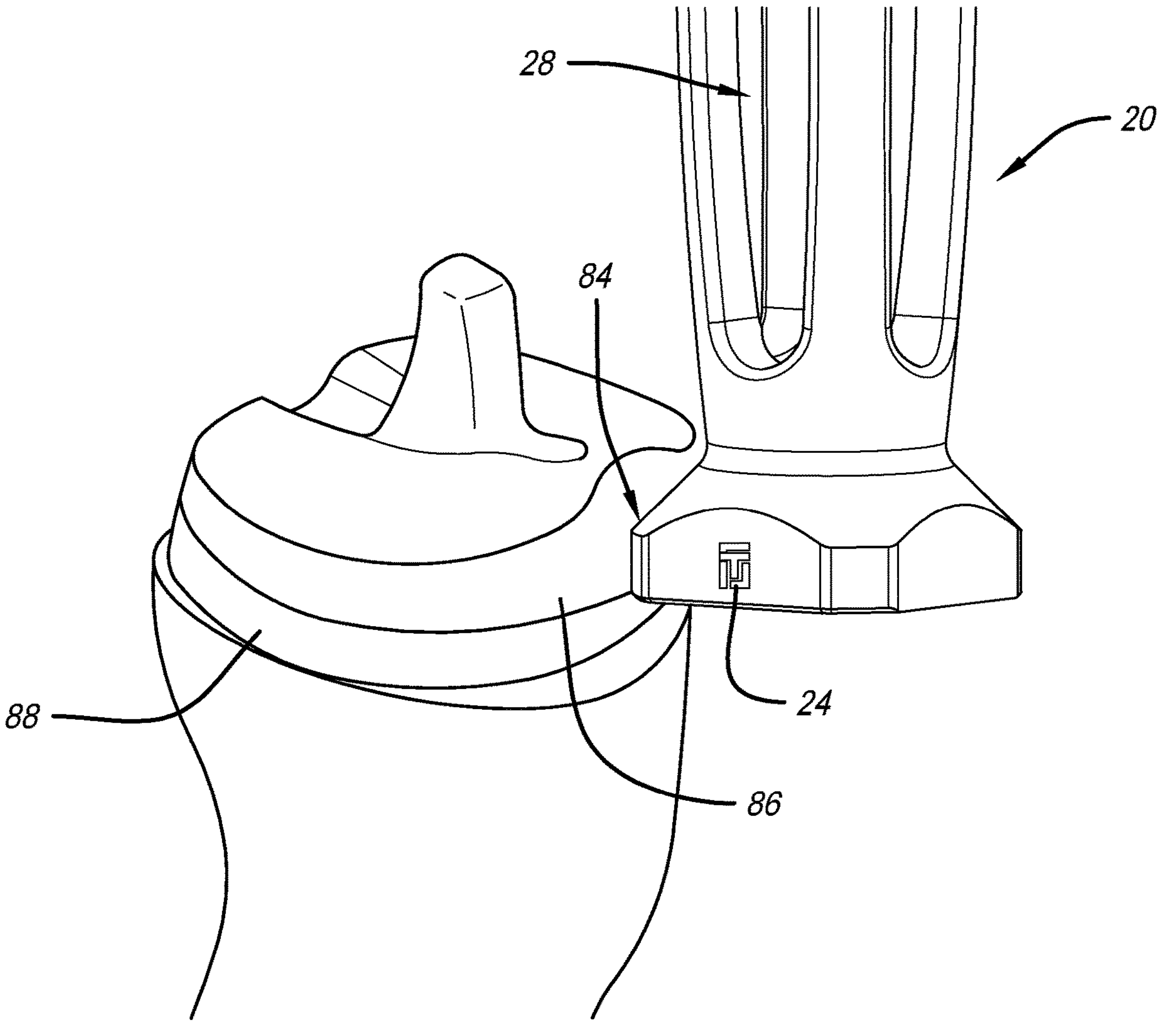
FIG. 11 is a perspective view of a tab coupled to a tibial insert for positioning the tibial insert on a tibial component.

As illustrated in FIG. 11, the dual-purpose orthopedic surgery instrument 20 may include a tab 84 (best shown in FIG. 3) that couples to a tibial insert 86. The tab 84 may generally extend outwardly perpendicular to the longitudinal axis of the elongated handle 22. The tab 84 may allow the surgeon to seat the tibial insert 86 on a tibial component 88. The tab 84 may further allow the surgeon to adjust the placement and/or alignment of the tibial insert 86. Alternatively, the tab 84 may be used to seat, position, and/or align femoral components, tibial components, trial components, or any component that does not need to be impacted into the bone.

Figure 16:
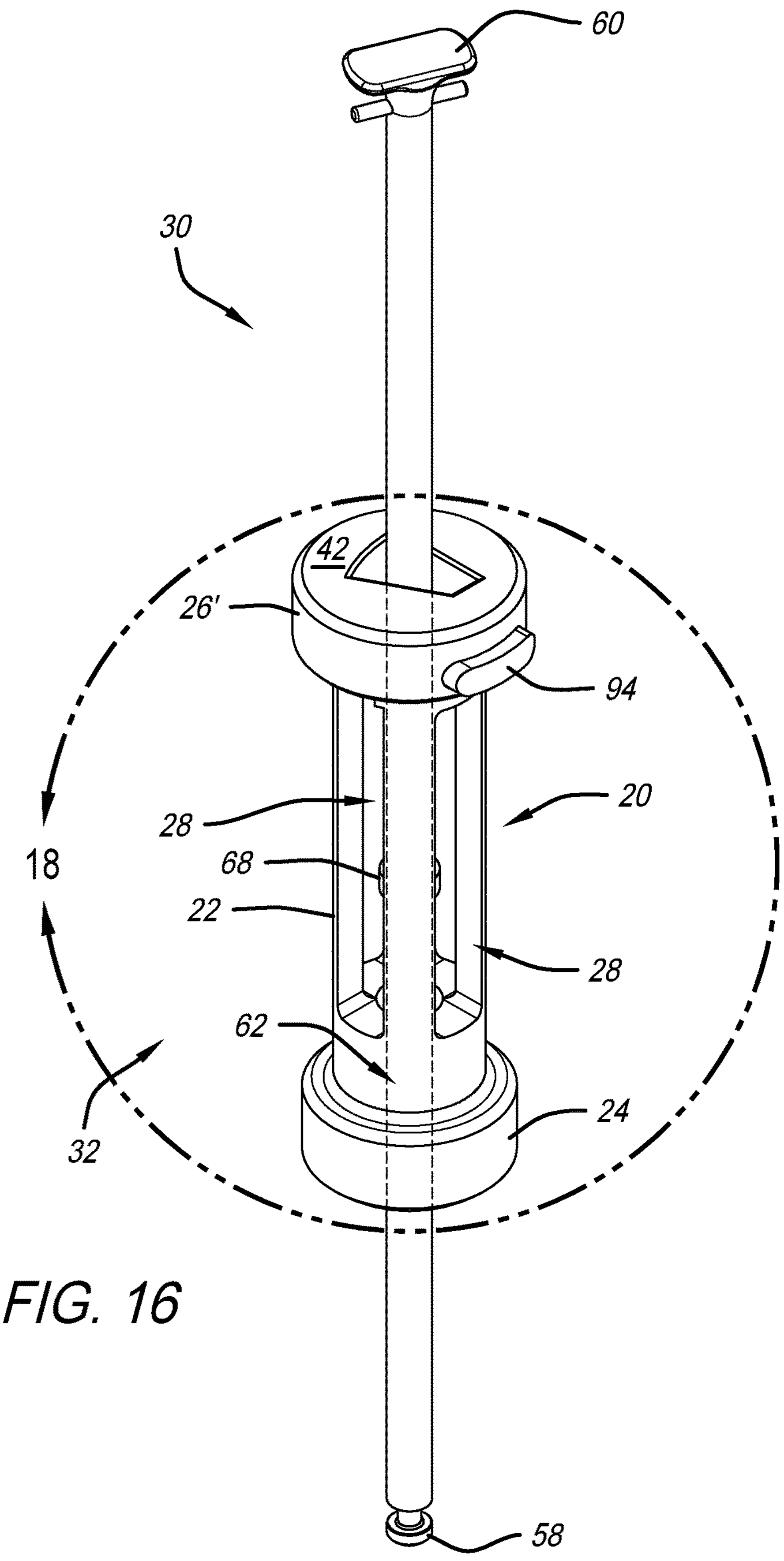
FIG. 16 is a perspective view of an alternative embodiment of the dual-purpose orthopedic surgery instrument having a locking slot selectively permitting coaxial pass-through insertion and retention of the extractor rod therethrough.
Figure 17A:
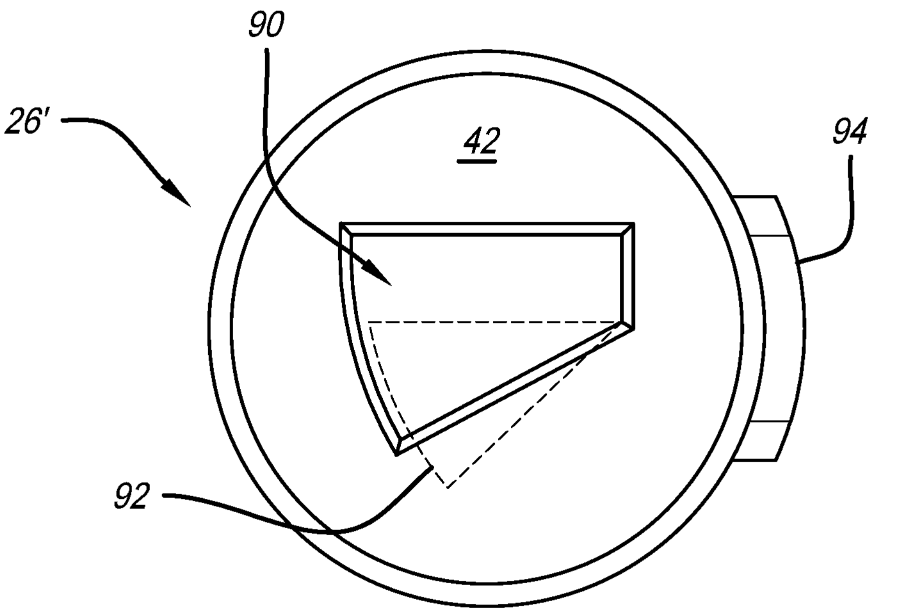
FIG. 17A is a top plan view of the locking slot in a closed position by way of a lever at least partially extending therein.

In an alternative embodiment illustrated in FIG. 16, the dual-purpose orthopedic instrument 20 may include an alternative strike block 26' that includes a locking slot 90 (FIGS. 17A-17B) configured to allow coaxial pass-through reception of the extractor rod 30 when in an open position, but constrain the extractor rod therein 30 when in a closed or locked position. More specifically in this respect, the alternative strike block 26' houses a movable lever 92 therein actuated by an externally accessible spring-actuated lever button 94. In FIG. 17A, the lever button 94 normally positions the lever 92 at least partially into the locking slot 90 when in a locked position. Here, when the locking slot 90 is in the closed position, the lever 92 obstructs part of the opening formed by the locking slot 90 such that the passable width therein is relatively smaller than the width of the stopper 68 of the extractor rod 30. As such, while the width of the extractor rod 30 is of a size that permits sliding movement within the locking slot 90 when in this locked position, the width of the stopper 68 is too large to pass therethrough while the lever 92 remains normally positioned therein as illustrated in FIG. 17A by the spring-biased lever button 94. Accordingly, the lever button 94 must be depressed to open the locking slot 90 to fully insert or remove the extractor rod 30 therefrom.

Figure 17B:
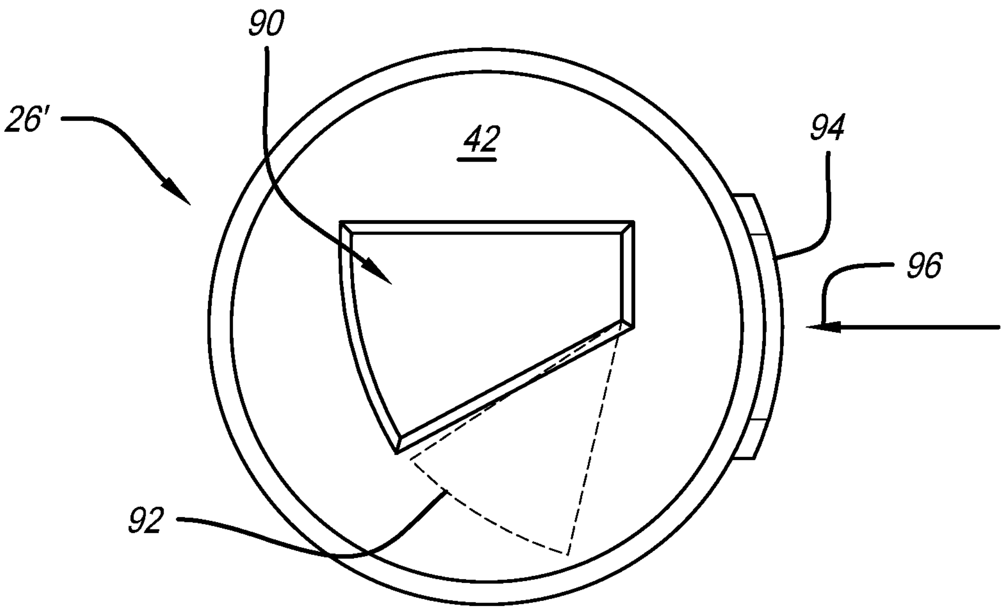
FIG. 17B is a top plan view of the locking slot in an open position by way of the lever being generally pivoted out from within the locking slot by an externally accessible spring-actuated lever button.

In this respect FIG. 17B illustrates depressing the lever button 94 generally along a directional arrow 96 to spring-actuate pivoting movement of the lever 92 within the alternative strike block 26'. When the lever button 94 is fully depressed as illustrated in FIG. 17B, the lever 92 pivots completely out from within the locking slot 90 so the lever 92 no longer provides any obstruction therein. Here, the locking slot 90 is now in an open position having a width large enough to allow coaxial pass-through reception or removal of the extractor rod 30 and its relatively larger diameter stopper 68. When in this position, the extractor rod 30 is no longer constrained within the dual-purpose orthopedic surgery instrument by the stopped 68, whereby the extractor rod 30 can be inserted and/or removed therefrom.

Figure 18:
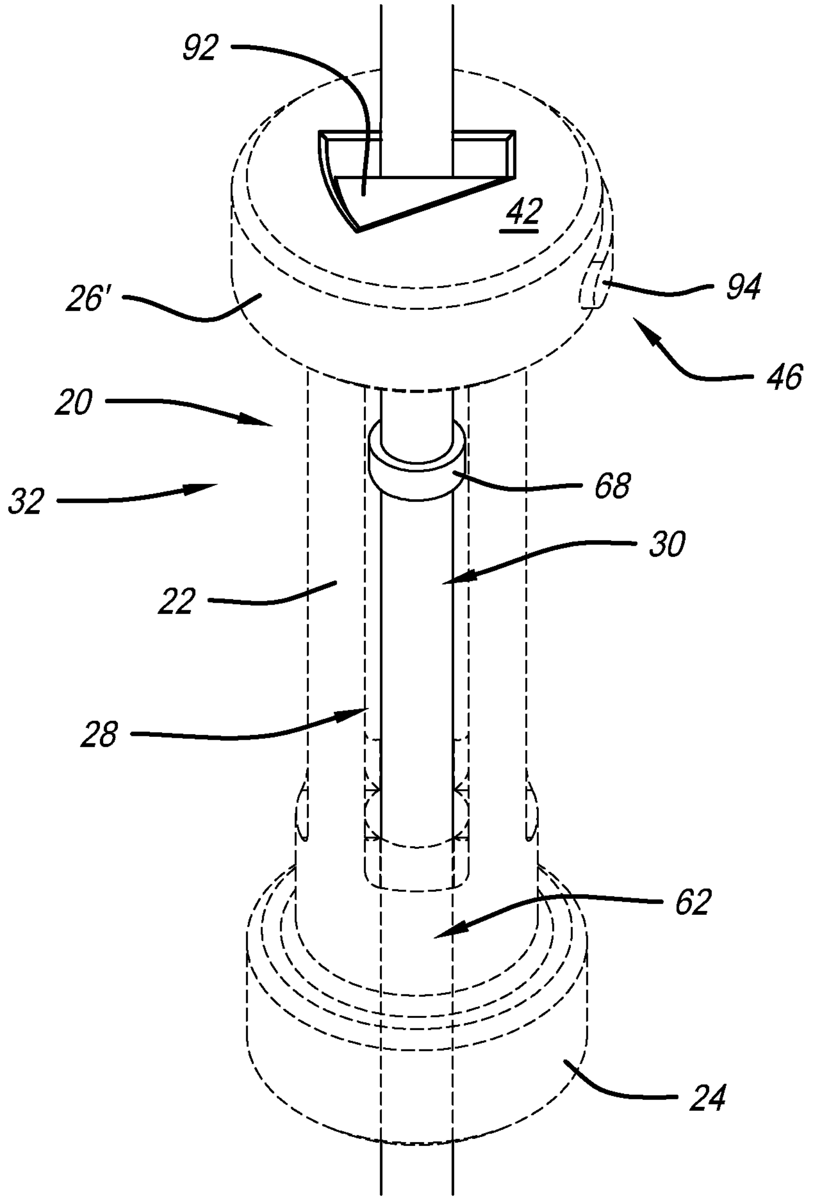
FIG. 18 is an enlarged perspective view taken about the circle 18 in FIG. 16, further illustrating the stopper of the extractor rod constrained within the slide channel when the locking slot is returned to the closed position after the stopper passes through the previously enlarged locking slot.

Accordingly, in this embodiment, to form the slap hammer 32 by way of engaging the dual-purpose orthopedic surgery instrument 20 with the extractor rod 30, the surgeon would first press the lever button 94 to move the lever 92 out of the locking slot 90 and then insert the tibial extractor 58 through the locking slot 90 and out through the impactor block 24. The open locking slot 90 allows the stopper 68 to pass through the strike block 26' and into the elongated channel 28. Releasing the button 94 allows the lever 92 to return to the closed position illustrated in FIG. 17A at least partially extending or blocking the locking slot 90. At this point, as best illustrated in FIG. 18, the stopper 68 is located below the strike block 26' and restrained within the elongated channel 28 because the width of the stopper 68 is relatively larger than the width of the bottom channel 62 and the locking slot 90. As when in this position, the extractor rod 30 is removably constrained between the impactor block 24 and the strike block 26', and the dual-purpose orthopedic surgery instrument 20 is in slidable relation relative to the extractor rod 30 for operation as the slap hammer 32. After use, the extractor rod 30 may be removed from the dual-purpose orthopedic instrument 20 by pressing the lever button 94 to reopen the locking slot 90 when the lever 92 pivots out from obstruction therein, and sliding the extractor rod 30 out of the locking slot 90 now that the stopper 68 has sufficient clearance to pass through the locking slot 90.

Lastly, an exemplary method of using the dual-purpose orthopedic surgery instrument 20 may include coupling the modular impactor head 34 to the impactor interface 25 of the impactor block 24, locating the modular impactor head 34 on the femoral trial 78, hitting the strike surface 42 with a hammer and impacting the femoral trial 78 into the distal end of a patient femur. The surgeon may then decouple the modular impactor head 34 and insert the extractor rod 30 in through the elongated channel 28 and into the bottom channel 62 and the recess 36, then tilt the extractor rod 30 into the keyed rod-receiving channel 52 (and optionally depressing the spring-loaded button 46 to facilitate opening the same), and then reposition the spring-loaded button 46 to lock the extractor rod 30 to the dual-purpose orthopedic surgery instrument 20. The femoral extractor 60 may then couple to the femoral trial 78 and the surgeon may slide the dual-purpose orthopedic surgery instrument 20 along the length of the elongated channel 28 for use as the slap hammer 32. Sliding the dual-purpose orthopedic surgery instrument 20 along the extractor rod 30 creates an impulse when the stopper 68 collides with either of the shoulders 69, 69'. The surgeon may repeat the sliding process until the femoral trial 78 is extracted from the distal end of the patient femur. The surgeon may then remove the extractor rod 30, couple the modular impactor head 34 to the impactor block 24, locate the modular impactor head 34 on an actual femoral implant component, and apply a force to the strike surface 42 to impact the actual femoral implant component into the distal end of the patient femur. Allowing the surgeon to perform all of these processes with a single dual-purpose orthopedic surgery instrument 20 reduces the number of individual devices required by the procedure and streamlines knee arthroplasty and/or knee revision.

Although several embodiments have been described in detail for purposes of illustration, various modifications may be made without departing from the scope and spirit of the invention. Accordingly, the invention is not to be limited, except as by the appended claims.

What is claimed is:

1. A dual-purpose orthopedic instrument, comprising:

an elongated body;

an impactor block formed from a first end of the elongated body selectively couplable with a modular impactor head;

a strike block formed from a second end of the elongated body including a strike surface for selectively receiving a strike force thereon; and an externally accessible channel having a size and shape for pass-through reception and select retention of an extractor rod therein, the elongated body usable as a modular impactor when the impactor block is selectively coupled with the impactor head and as a weight of a slap hammer when selectively coupled with the extractor rod in slidable relation relative thereto;

wherein the first end includes a tapered channel having a size and shape for at least partial reception of a first end of the extractor rod at an angle offset from a longitudinal axis of the elongated body while a second end of the extractor rod extends out from the externally accessible channel; and wherein the second end includes a receiving channel having a size and shape for tilt-in insertion of the second end of the extractor rod through the externally accessible channel.

2. The orthopedic instrument of claim 1, wherein at least a portion of the extractor rod is keyed for insertion within the receiving channel in a predetermined orientation.

3. The orthopedic instrument of claim 1, wherein at least a portion of the extractor rod includes a pair of planar surfaces located along a length thereof positioned to abut a commensurate pair of interior planar surfaces of the receiving channel when the extractor rod is inserted therein, the abutting planar surfaces thereby prevent coaxial rotation of the extractor rod relative to the elongated body.

4. The orthopedic instrument of claim 1, wherein, upon full insertion of the extractor rod within the receiving channel, the extractor rod resides substantially coaxial within the externally accessible channel and in slidable relation with within the elongated body.

5. The orthopedic instrument of claim 4, wherein the extractor rod includes a stopper relatively smaller than the externally accessible channel yet relatively larger than the tapered channel and the receiving channel, thereby removably retaining the extractor rod within the elongated body between the first end and the second end.

6. The orthopedic instrument of claim 5, wherein the externally accessible channel comprises an arcuate channel and the stopper comprises a size and shape relatively larger than an upper section and a lower section of the arcuate channel and relatively smaller than a middle section of the arcuate channel for pass-through reception therewith.

7. The orthopedic instrument of claim 6, wherein the extractor rod comprises a length at least partially residing within the first end when the stopper is seated within the tapered channel and at least partially residing within the second end when the stopper is in contact with the first end.

8. The orthopedic instrument of claim 1, including a button generally biasing a lock in a normal closed position at least partially enclosing the receiving channel thereby preventing slide-out removal of the second end of the extractor rod therefrom.

9. The orthopedic instrument of claim 8, wherein the lock includes a chamfered latch self-actuable by the second end of the extractor rod.

10. The orthopedic instrument of claim 8, wherein the button comprises a spring-actuated button at least partially residing within an internal enclosure of the strike block.

11. The orthopedic instrument of claim 1, wherein the externally accessible channel includes a locking slot formed from a portion of one of the impactor block or the strike block.

12. The orthopedic instrument of claim 11, including a lever normally positioned within the externally accessible channel generally blocking passthrough movement of an outwardly projecting stopper formed along a length of the extractor rod.

13. The orthopedic instrument of claim 12, including a button actuable to selectively displace the lever out from within the externally accessible channel, thereby permitting the outwardly projecting stopper to pass therethrough.

14. The orthopedic instrument of claim 1, wherein the modular impactor head includes an aperture having a size and shape for pass-through reception of at least a portion of the extractor rod.

15. The orthopedic instrument of claim 1, wherein the strike surface comprises an angled surface offset from a longitudinal axis of the elongated body or a non-planar strike surface selected from the group consisting of a curved surface, a spherical surface, and a spheroidal surface.

16. The orthopedic instrument of claim 1, wherein the elongated body includes a tab outwardly extending therefrom selectively couplable to an orthopedic component.

17. The orthopedic instrument of claim 1, wherein the impactor block includes an impactor interface having a size and shape for select coupling to the impactor head via snap-fit engagement, threaded engagement, or slide-fit engagement.

18. A slap hammer, comprising:

a handle having an externally accessible channel;

a first end of the handle having a tapered channel formed therein;

a second end of the handle having a receiving channel formed therein; and an extractor rod having an outwardly extending stopper formed along a length thereof, the stopper being of a size and shape relatively smaller than the externally accessible channel while being relatively larger than the tapered channel and the receiving channel, the extractor rod being at least partially insertable into the tapered channel at an angle offset from a longitudinal axis of the handle and tiltable therein to pass the stopper through the relatively larger externally accessible channel for insertion of the extractor rod into the receiving channel in coaxial relation relative to the handle, the handle thereafter movable along the length of the extractor rod as a weight of the slap hammer constrained by the stopper between the first end and the second end.

19. The slap hammer of claim 18, wherein the first end comprises an impactor block selectively couplable with a modular impactor head and the second end comprises a strike block having a strike surface for selectively receiving a strike force thereon.

20. The slap hammer of claim 18, wherein at least a portion of the extractor rod is keyed for insertion within the receiving channel in a predetermined orientation.

21. The slap hammer of claim 18, wherein at least a portion of the extractor rod includes a pair of planar surfaces located along a length thereof positioned to abut a commensurate pair of interior planar surfaces of the receiving channel, the abutting planar surfaces thereby prevent coaxial rotational movement of the extractor rod relative to the elongated body.

22. The slap hammer of claim 18, wherein the externally accessible channel comprises an arcuate channel, the stopper being relatively larger than an upper section and a lower section of the arcuate channel and relatively smaller than a middle section of the arcuate channel.

23. The slap hammer of claim 18, wherein the extractor rod at least partially resides within the first end when the stopper is seated within the tapered channel and at least partially resides within the second end when the stopper is in contact with the first end.

24. The slap hammer of claim 18, including a button generally biasing a lock in a normal closed position at least partially enclosing the receiving channel thereby preventing slide-out removal of the extractor rod therefrom.

25. The slap hammer of claim 24, wherein the lock includes a chamfered latch self-actuable by the extractor rod.

26. The slap hammer of claim 24, wherein the button comprises a spring-actuated button at least partially residing within an internal enclosure of the first end.

27. A dual-purpose orthopedic instrument, comprising:

an elongated body;

an impactor block formed from a first end of the elongated body selectively couplable with a modular impactor head;

a strike block formed from a second end of the elongated body including a strike surface for selectively receiving a strike force thereon;

an externally accessible channel having a size and shape for pass-through reception and select retention of an extractor rod therein, the elongated body usable as a modular impactor when the impactor block is selectively coupled with the impactor head and as a weight of a slap hammer when selectively coupled with the extractor rod in slidable relation relative thereto, wherein the externally accessible channel includes a locking slot formed from a portion of one of the impactor block or the strike block; and a lever normally positioned within the externally accessible channel generally blocking passthrough movement of an outwardly projecting stopper formed along a length of the extractor rod.

28. The orthopedic instrument of claim 27, wherein the first end includes a tapered channel having a size and shape for at least partial reception of a first end of the extractor rod at an angle offset from a longitudinal axis of the elongated body while a second end of the extractor rod extends out from the externally accessible channel.

29. The orthopedic instrument of claim 27, wherein the externally accessible channel includes a locking slot formed from a portion of one of the impactor block or the strike block.

30. The orthopedic instrument of claim 27, wherein the modular impactor head includes an aperture having a size and shape for pass-through reception of at least a portion of the extractor rod.

31. The orthopedic instrument of claim 27, wherein the strike surface comprises an angled surface offset from a longitudinal axis of the elongated body or a non-planar strike surface selected from the group consisting of a curved surface, a spherical surface, and a spheroidal surface.

32. A dual-purpose orthopedic instrument, comprising:

an elongated body;

an impactor block formed from a first end of the elongated body selectively couplable with a modular impactor head, wherein the impactor block includes an impactor interface having a size and shape for select coupling to the impactor head via snap-fit engagement, threaded engagement, or slide-fit engagement;

a strike block formed from a second end of the elongated body including a strike surface for selectively receiving a strike force thereon; and an externally accessible channel having a size and shape for pass-through reception and select retention of an extractor rod therein, the elongated body usable as a modular impactor when the impactor block is selectively coupled with the impactor head and as a weight of a slap hammer when selectively coupled with the extractor rod in slidable relation relative thereto.

33. The orthopedic instrument of claim 32, wherein the first end includes a tapered channel having a size and shape for at least partial reception of a first end of the extractor rod at an angle offset from a longitudinal axis of the elongated body while a second end of the extractor rod extends out from the externally accessible channel.

34. The orthopedic instrument of claim 32, wherein the externally accessible channel includes a locking slot formed from a portion of one of the impactor block or the strike block.

35. The orthopedic instrument of claim 32, wherein the modular impactor head includes an aperture having a size and shape for pass-through reception of at least a portion of the extractor rod.

36. The orthopedic instrument of claim 32, wherein the strike surface comprises an angled surface offset from a longitudinal axis of the elongated body or a non-planar strike surface selected from the group consisting of a curved surface, a spherical surface, and a spheroidal surface.

* * * * *